United States Patent
Bernstein et al.

(10) Patent No.: US 6,511,438 B2
(45) Date of Patent: Jan. 28, 2003

(54) APPARATUS AND METHOD FOR DETERMINING AN APPROXIMATION OF THE STROKE VOLUME AND THE CARDIAC OUTPUT OF THE HEART

(75) Inventors: Donald P. Bernstein, Rancho Santa Fe, CA (US); Markus J. Osypka, Knuellwald (DE)

(73) Assignee: Osypka Medical GmbH, Berlin (DE)

( * ) Notice: Subject to any disclaimer, the term of this patent is extended or adjusted under 35 U.S.C. 154(b) by 56 days.

(21) Appl. No.: 09/824,942

(22) Filed: Apr. 3, 2001

(65) Prior Publication Data

US 2002/0193689 A1 Dec. 19, 2002

(51) Int. Cl.[7] .............................. A61B 5/04; A61B 5/029; A61B 5/0295
(52) U.S. Cl. .................... 600/526; 600/506; 600/509
(58) Field of Search ............................ 600/504, 506, 600/507, 508, 509, 512, 513, 526

(56) References Cited

U.S. PATENT DOCUMENTS

| | | | |
|---|---|---|---|
| 3,340,867 A | 9/1967 | Kubicek et al. | 600/526 |
| 4,450,527 A | 5/1984 | Sramek | 600/484 |
| 4,562,843 A * | 1/1986 | Djordjevich et al. | 600/485 |
| 4,807,638 A | 2/1989 | Sramek | 600/485 |
| 4,836,214 A | 6/1989 | Sramek | 600/506 |
| 4,953,556 A | 9/1990 | Evans | 600/484 |
| 5,103,828 A | 4/1992 | Sramek | 600/481 |
| 5,178,154 A | 1/1993 | Ackmann et al. | 600/526 |
| 5,309,917 A | 5/1994 | Wang et al. | 600/508 |
| 5,316,004 A | 5/1994 | Chesney et al. | 600/485 |
| 5,423,326 A * | 6/1995 | Wang et al. | 600/526 |
| 5,469,859 A | 11/1995 | Tsoglin et al. | 600/536 |
| 5,503,157 A | 4/1996 | Sramek | 600/506 |
| 5,505,209 A * | 4/1996 | Reining | 600/547 |
| 5,529,072 A * | 6/1996 | Sramek | 600/506 |
| 5,685,316 A | 11/1997 | Schookin et al. | 600/526 |
| 5,782,774 A | 7/1998 | Shmulewitz | 600/547 |
| 5,791,349 A | 8/1998 | Shmulewitz | 600/547 |
| 6,016,445 A | 1/2000 | Baura | 600/547 |
| 6,058,325 A | 5/2000 | Baura | 607/8 |
| 6,095,987 A | 8/2000 | Shmulewitz et al. | 600/547 |
| 6,102,869 A | 8/2000 | Meier et al. | 600/506 |
| 6,161,038 A * | 12/2000 | Schookin et al. | 600/519 |
| 6,186,955 B1 | 2/2001 | Baura | 600/526 |

OTHER PUBLICATIONS

Wallace, Arthur W.; "Endotracheal Cardiac Output Monitor"; Anesthesiology; vol. 92: 178–89; Jan. 2000.

* cited by examiner

Primary Examiner—Carl Layno
(74) Attorney, Agent, or Firm—Martin & Ferraro, LLP

(57) ABSTRACT

The invention relates to an apparatus and a method for determining an approximate value for the stroke volume and the cardiac output of a person's heart. The apparatus and method employ a measured electrical impedance, or admittance, of a part of a person's body, namely, the thorax. This part of a person's body is chosen because its electrical impedance, or admittance, changes with time as a consequence of the periodic beating of the heart. Accordingly, the measured electrical admittance or impedance can provide information about the performance of the heart as a pump.

140 Claims, 10 Drawing Sheets

APPARATUS AND METHOD FOR DETERMINING AN APPROXIMATION OF THE STROKE VOLUME AND THE CARDIAC OUTPUT OF THE HEART

FIELD OF THE INVENTION

The invention relates to an apparatus and a method for determining an approximate value for the stroke volume and the cardiac output of a person's heart. The apparatus and method employ a measured electrical impedance, or admittance, of a part of a person's body, namely, the thorax. This part of a person's body is chosen because its electrical impedance, or admittance, changes with time as a consequence of the periodic beating of the heart. Accordingly, the measured electrical admittance or impedance can provide information about the performance of the heart as a pump.

RELATED PRIOR ART

In 1966, Kubicek et al. were the first to design a clinically applicable device, capable of determining the stroke volume (SV) by non-invasive, electrical means. The Kubicek method is disclosed in the article by Kubicek et al., Development and Evaluation of an Impedance Cardiac Output System, Aerospace Medicine 1966, pp 1208–1212, and in U.S. Pat. No. 3,340,867 which are both incorporated herein by reference. (see also U.S. Pat. No. 5,178,154 to Ackmann et al, U.S. Pat. No. 5,316,004 to Chesney et al, U.S. Pat. No. 4,953,556 to Evans, U.S. Pat. No. 5,685,316 to Schookin et al, U.S. Pat. No. 5,505,209 to Reining, U.S. Pat. No. 5,529,072 to Sramek, U.S. Pat. No. 5,503,157 to Sramek, U.S. Pat. No. 5,469,859 to Tsoglin et al, U.S. Pat. No. 5,423,326 to Wang et al, and U.S. Pat. No. 5,309,917 to Wang et al.)

When a tetrapolar array of circumferential band electrodes is placed at the base of the neck and about the circumference of the lower chest, at the level of the xiphoid process, and a constant magnitude alternating current (AC) is injected through the upper cervical and lower thoracic band electrodes, a voltage, proportional to the thoracic electrical impedance (or reciprocally proportional to the admittance), is measured between the inner cervical and thoracic band electrodes. The portion of the cardiac synchronous impedance change, $\Delta Z(t)$, temporally concordant with stroke volume, was ascribed solely and uniquely to volume (plethysmographic) changes of the aorta during expansion and contraction over the heart cycle.

In the article by Woltjer H. H. et al. (The technique of impedance cardiography. Eur Heart J 1977; 18: 1396–1403), the Kubicek model is explained as follows. The aorta is considered a cylinder of length L, equal to the distance between the voltage sensing electrodes. The thorax, exclusive of the aorta, is considered a cylinder of length L, equal to aortic length, and of cross-sectional area (CSA), equal to the cross-sectional area of the thorax measured at the xiphoid level. The blood-filled aorta is assumed to have a constant specific electrical resistance equal to that of stationary blood, $\rho$. The thoracic encompassing cylinder is assumed to be homogeneously perfused with blood of specific resistance $\rho$. The aorta and the thoracic encompassing cylinder are assumed to be analogous to parallel electrical conductors.

It was accepted by Kubicek that, according to Nyboer (J. Electrical impedance plethysmography. A physical and physiologic approach to peripheral vascular study. Circulation 1950; 2: 811–821), the portion of $\Delta Z(t)$, temporally concordant with SV, represented simultaneous inflow and outflow of blood over the systolic portion of the heart cycle. Thus, determining the area underneath the systolic portion of $\Delta Z(t)$ was assumed not to represent net volume inflow across the aortic segment under electrical interrogation. Thus, an extrapolation procedure was proposed, utilizing the maximum forward systolic slope of $\Delta Z(t)$. In order to compensate for aortic outflow, the maximum forward slope, analogous to peak flow, was stipulated to be constant throughout the systolic ejection interval. The maximum forward systolic upslope represents the peak, or maximum rate of change of impedance, i.e.

$$\left(\frac{dZ(t)}{dt}\right)_{MAX}.$$

Instead of measuring the slope directly, as proposed by Nyboer, Kubicek electronically differentiated $\Delta Z(t)$ into $dZ(t)/dt$. Thus, the peak systolic magnitude of $dZ(t)/dt$ is $$\left(\frac{dZ(t)}{dt}\right)_{MAX}.$$

In order to derive stroke volume (SV), Kubicek multiplied the peak rate of change of impedance by systolic flow time of the left ventricle, $T_{LVE}$.

According to Kubicek $$SV = V_{eff} \cdot \frac{\left(\frac{dZ(t)}{dt}\right)_{MAX}}{Z_0} \cdot T_{LVE} = \rho \frac{L^2}{Z_0} \cdot \frac{\left(\frac{dZ(t)}{dt}\right)_{MAX}}{Z_0} \cdot T_{LVE},$$

wherein $Z_0$ is the quasi-static portion of the measured impedance Z, and wherein $$\left(\frac{dZ(t)}{dt}\right)_{MAX}$$

is the peak value of the (inverted) first time-derivative of $\Delta Z(t)$, which corresponds to the maximum forward systolic upslope of $\Delta Z(t)$. Note that in this context, by peak magnitude, the maximum absolute amplitude is stipulated. In fact, during systole, the impedance decreases such that the sign of $\Delta Z(t)$ is negative. Hence, correctly stated, $$\left(\frac{dZ(t)}{dt}\right)_{MAX}$$

is the minimum of the time-derivative of $\Delta Z(t)$, i.e.

$$\left(\frac{dZ(t)}{dt}\right)_{MIN}.$$

Furthermore, in the above formula, $T_{LVE}$ is the left ventricular ejection time, i.e. the time between opening and closure of the aortic valve, also referred to as systolic flow time. The volume $$V_{EFF} = \rho \cdot \frac{L^2}{Z_0}$$

is the volume of electrically participating thoracic tissue (VEPT), wherein $\rho$ is the specific resistance of stationary blood, which Kubicek assumed to be 150 Ωcm, and L is the distance between the voltage-sensing electrodes which are applied to the neck and thorax.

By virtue of rigid theoretical constraints, the Kubicek method, and its derivatives, consider volume changes in the aorta, i.e. plethysmographic changes, to be the sole contributor to $$\left(\frac{dZ(t)}{dt}\right)_{MAX}.$$

Consequently, $\Delta Z(t)$ is assumed to represent the time-variable volumetric expansion and recoil of the aorta. Thus, its time-derivative, $dZ(t)/dt$, represents an ohmic equivalent of the rate of change of aortic volume. This would also imply that $$\left(\frac{dZ(t)}{dt}\right)_{MAX},$$

measured in [Ω/s], is directly proportional to peak flow [mL/s] and peak velocity [cm/s].

It is widely believed that the assumptions made in the Kubicek model are generally valid, i.e. that the increased aortic volume during mechanical systole leads to the decrease in the thoracic impedance. Since Kubicek assumed a directly proportional, i.e. linear, relationship between SV and $$\left(\frac{dZ(t)}{dt}\right)_{MAX}$$

times $T_{LVE}$, it is usually believed that $$\left(\frac{dZ(t)}{dt}\right)_{MAX}$$

is analogous and proportional to peak flow, or peak rate of change of aortic volume. Therefore, subsequent improvements focused only on a better definition and modeling of $V_{EFF}$.

For example, Sramek developed a formula according to which $$V_{EFF} = \frac{L^3}{4.25}$$

(see U.S. Pat. No. 4,450,527 which is incorporated herein by reference).

In a later iteration, Sramek approximated L as 17% of the person's height h. Thus, Sramek proposed the equation $$SV = \frac{(0.17h)^3}{4.25} \cdot \frac{\left(\frac{dZ(t)}{dt}\right)_{MAX}}{Z_0} \cdot T_{LVE}$$

Bernstein (Bernstein D. P., A new stroke volume equation for thoracic electrical bioimpedance. Crit Care Med 1986; 14: 904–909) introduced a factor δ accounting for the person's weight deviation from ideal (as determined from the Metropolitan Life Insurance tables), corrected for blood volume, normalized to deviation from ideal body weight. Otherwise, Sramek's model remained unchanged, and Bernstein proposed the formula $$SV = \delta \cdot \frac{(0.17h)^3}{4.25} \cdot \frac{\left(\frac{dZ(t)}{dt}\right)_{MAX}}{Z_0} \cdot T_{LVE}$$

Despite these various efforts for improving the determination of the stroke volume, the stroke volume could not be correctly predicted across a wide range of subjects in health and disease.

In particular, in the following cases, the Sramek-Bernstein equation generally results in an overestimation of the true predicted stroke volume: children and healthy young adults; underweight individuals; tall, thin adults.

According to Spiering et al (Comparison of impedance cardiography and dye dilution methods for measuring cardiac output. Heart 1998; 79: 437–441), the use of the Sramek-Bernstein equation generally results in an underestimation of the true predicted stroke volume in the following cases: elderly adults, obese individuals; individuals with sepsis, acute lung injury or pulmonary edema; and during exercise.

SUMMARY OF THE INVENTION

It is therefore an object of the invention to provide apparatus and method that determines the stroke volume accurately for individuals of all ages in health and disease states.

The invention considers the absolute peak rate of change of impedance, $$\left|\left(\frac{dZ(t)}{dt}\right)_{MIN}\right|,$$

to be the ohmic equivalent of peak aortic blood acceleration [mL/s²], or peak rate of change of aortic blood velocity. As a consequence, $\Delta Z(t)$, in earliest systole, is related to hemorheologic (blood flow) changes, not plethysmographic (volume) changes. Thus, the new apparatus can be described as an 'electrical velocimeter', or the method incorporated as 'electrical velocimetry'.

Consequently, the measured value of $$\left|\left(\frac{dZ(t)}{dt}\right)_{MIN}\right|$$

cannot be implemented directly into SV calculation. Theoretically, $$\left|\left(\frac{dZ(t)}{dt}\right)_{MIN}\right|$$

must be integrated in order to obtain an ohmic equivalent for blood velocity. In summary, the invention mandates that the part of the previous art related to $$\frac{\left|\left(\frac{dZ(t)}{dt}\right)_{MIN}\right|}{Z_0}$$

be changed.

Hence, the apparatus and method according to the invention employ no underlying modeling or theoretical assumptions of the Kubicek, or any other subsequent, plethysmographic approaches.

According to theory derived from basic science (and published as Sakamoto K, Kanai K. Electrical characteristics of flowing blood. IEEE Trans Biomed Eng 1979; 26: 686–695; Visser K R. Electrical properties of flowing blood and impedance cardiography. Ann Biomed Eng 1989; 17: 463–473; Lamberts R et al. Impedance cardiography. Assen, The Netherlands: Van Gorcum 1984; 84–85; and Matsuda Y et al. Assessment of left ventricular performance in man with impedance cardiography. Jap Circ J 1978; 42: 945-954), the change of blood resistivity, and the rate of change of blood resistivity, can be normalized for corrected flow time, FTC, $$FT_C = \frac{T_{LVE}}{T_{RR}^m},$$

where $T_{LVE}$ equals the left-ventricular ejection time (known also as systolic flow time), divided by a root of $T_{RR}$, where $T_{RR}$ equals the value for the RR interval (cycle time) in seconds.

With $V_{EFF}$ defined as the effective volume of electrical participating thoracic tissue ($[V_{EFF}]$=ml), the stroke volume SV, according to the invention, is calculated according to the formula $$SV = V_{EFF} \cdot C_1 \left( \frac{\left|\left(\frac{dZ(t)}{dt}\right)_{MIN}\right|}{Z_0} \right)^n \cdot \left(\frac{1}{T_{RR}}\right)^m \cdot T_{LVE}$$

with $0.15 < n < 0.8$ and $0 \leq m \leq 1.5$, and wherein $C_1$ is a constant which is necessary if $n+m \neq 1$ in order to adjust the units of the measured values in the formula such that the stroke volume is obtained in milliliters. $C_1$ need not have a numerical value different from 1.

A preferred case is that $n=1-m$. Then, $C_1=1$.
The most preferred case is $n=m=0.5$. Then, $$FT_C = \frac{T_{LVE}}{\sqrt{T_{RR}}}.$$

Other objects, features and advantages of the invention will become apparent from the following description of a preferred embodiment of the invention.

DETAILED DESCRIPTION OF THE INVENTION

Principally, an alternating electrical field is applied to a thoracic volume forcing an alternating current (AC) to flow in parallel to the direction of aortic blood flow, i.e. vertically between neck and lower thorax. The current of known magnitude causes, in the direction of the electrical field, a voltage drop, which is proportional to the product of thoracic impedance and current applied.

Figure 1:
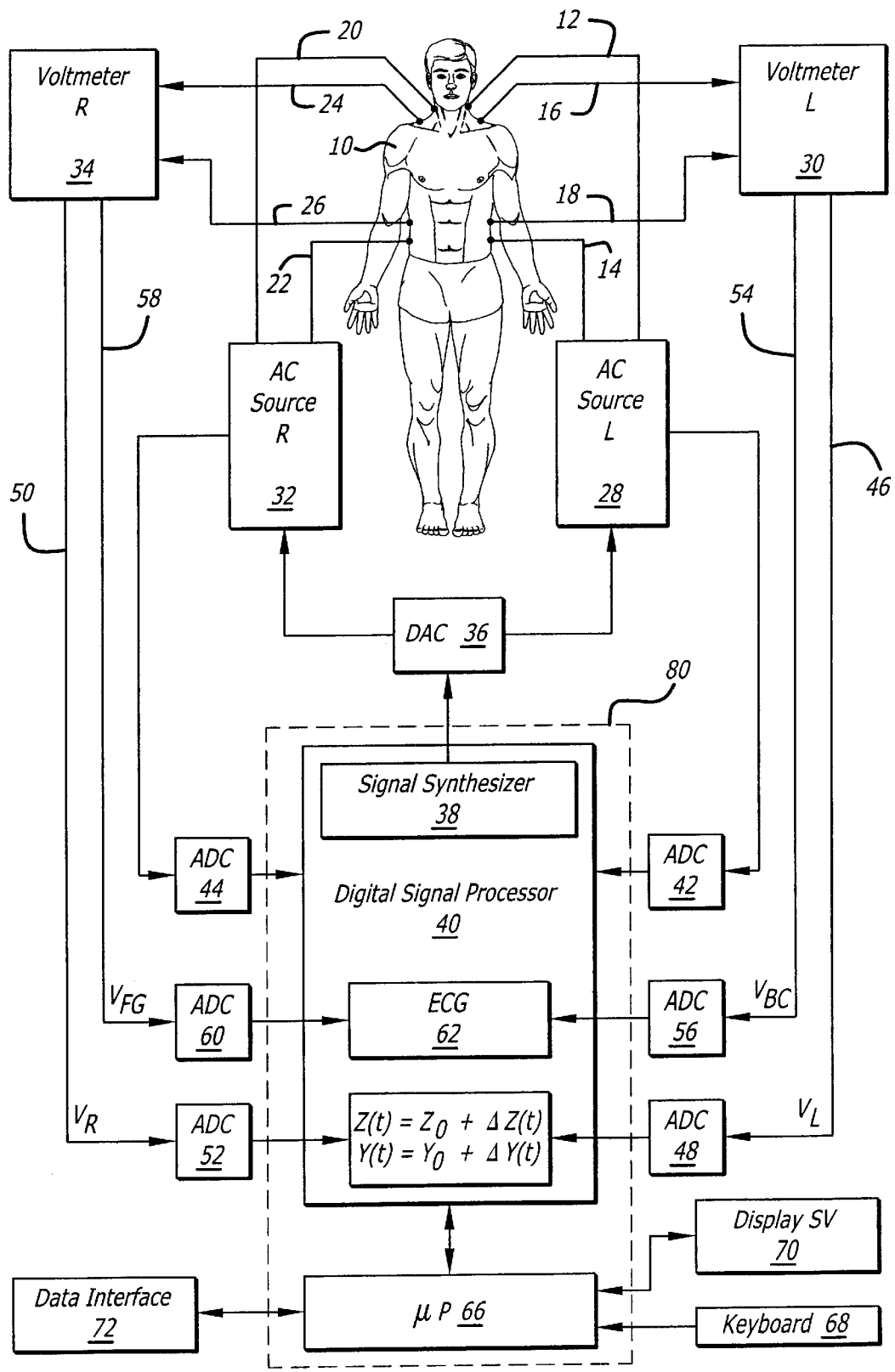
FIG. 1 is a schematic diagram depicting the apparatus, which uses on a subject's left and right side of the thorax, each, a tetrapolar surface electrode array, an alternating current (AC) source and a voltmeter.

FIG. 1 schematically shows an apparatus according to the present invention, and its electrical interface with a subject 10. For the measurement of transthoracic electrical bio-impedance (or bioadmittance), a tetrapolar surface electrode array (with electrodes 12, 14 for AC application, and electrodes 16, 18 for voltage sensing) is applied to the subject's left side, and another tetrapolar electrode array (with electrodes 20, 22 for AC application, and electrodes 24, 26 for voltage sensing) to the subject's right side.

The left sided electrode array includes two current electrodes 12, 14, which are connected to an AC Source L 28, and two voltage sensing electrodes 16, 18, which are connected to Voltmeter L 30. One voltage sensing electrode (16) is placed at the base of the neck, the other one (18) the lower thorax, at the level of the xiphoid process. The current electrodes (12, 14) are placed respectively, in the vertical direction, above and below the voltage sensing electrodes (16, 18).

The right sided electrode array includes two current electrodes 20, 22, which are connected to an AC Source R 32, and two voltage sensing electrodes 24, 26, which are connected to Voltmeter R 34. One voltage sensing electrode (24) is placed at the base of the neck, the other one (26) the lower thorax, at the level of the xiphoid process. The current electrodes (20, 22) are placed respectively, in the vertical direction, above and below the voltage sensing electrodes (24, 26).

AC Source L 28 and AC Source R 32 are voltage-controlled current sources (VCCS). Each VCCS provides an alternating current (AC), which is measured via Analog/Digital Converters 42, 44. Alternatively, the magnitude of the alternating current can be held constant, and the Analog/Digital Converters 42, 44 can be omitted. A Digital/Analog Converter (DAC) 36 provides an output that controls the AC Source L 28 and AC Source R 32. The Digital/Analog Converter (DAC) 36 itself is controlled by a Signal Synthesizer 38. The Signal Synthesizer 38 is implemented via a lookup-table in the memory of a Digital Signal Processor 40 as part of a Processing Unit 80 (indicated by dashed lines). Alternatively, a Direct Digital Synthesizer (DDS, not shown) can provide the functions of DAC 36 and Signal Synthesizer 38. The Processing Unit 80 recognizes AC magnitude and phase of each VCCS.

The voltages measured by the Voltmeters L 30 and R 34 do not only contain a signal caused by the AC applied, but also a signal component from which an electrocardiogram (ECG) can be derived. The application of filters separates the AC related and ECG related signal components. The AC related signal component is proportional to the product of current applied and the impedance (which is unknown). In the case that the currents applied are of constant magnitude, the voltage $V_L$ 46 obtained by voltmeter L 30, and digitized by the analog/digital converter 48, is directly proportional to the unknown impedance of the left hemi-thorax, $Z_L(t)$ (or reciprocally proportional to the unknown admittance, $Y_R(t)$). With the AC magnitude held constant, the voltage $V_R$ 50 obtained by voltmeter R 34, and digitized by the analog/digital converter 52, is directly proportional to the unknown impedance of the right hemi-thorax, $Z_R(t)$ (or reciprocally proportional to the unknown admittance, $Y_R(t)$). The Processing Unit 80 determines Z(t) by averaging $Z_L(t)$ and $Z_R(t)$, or Y(t) by averaging $Y_L(t)$ and $Y_R(t)$. Alternatively, the voltage $V_L$ 46 sensed between electrodes 16 and 18 (left side) and the voltage $V_R$ 50 sensed between the electrodes 24 and 26 (right side) can be summed, or averaged, prior to the voltmeters, requiring then only one analog/digital converter.

A demodulation of the AC related signal component is required in order to extract the impedance related information from the AC carrier signal. Demodulation of the voltages obtained from the thorax is described, for example, by Osypka and Schafer (Impedance cardiography: Advancements in system design. Proceedings of the X. International Conference on Electrical Bio-Impedance (ICEBI). Barcelona, Spain, Apr. 5–9, 1998), utilizing phase-sensitive detectors. With respect to FIG. 1, demodulation is an integral part of the voltmeters 30, 34. Alternatively, demodulation is performed by utilizing digital correlation technique, which is accomplished, for example, by the Digital Signal Processor 40 (Osypka et al. Determination of electrical impedances of tissue at a frequency range of 5 Hz to 20 KHz by digital correlation technique. Proceedings of the V. Mediterranean Conference on Medical and Biological Engineering (MEDICON). Patras, Greece, Aug. 29–Sep. 1, 1989).

Voltmeter L 30 also obtains the electrocardiogram (ECG) vector $V_{BC}$, measured between the left-sided sensing electrodes 16 and 18, which is digitized by an analog/digital converter 56 and fed to the Processing Unit 80. Voltmeter R obtains the ECG vector $V_{FG}$, measured between the right-sided sensing electrodes 24 and 26, which is digitized by an analog/digital converter 60 and fed to the Processor Unit 80.

It is understood that more ECG vectors can be obtained by paired combination of sensing electrodes between the left hemi-thorax (16, 18) and the right hemi-thorax (24, 26). The measurement of additional ECG vectors requires additional voltmeters and analog/digital converters (ADC) connected to the Processing Unit.

The Processing Unit automatically, or the operator manually, determines the most appropriate ECG vector, or superimposes several ECG vectors to achieve a resulting mean, or reference ECG 62. Alternatively, the outputs of several voltmeters are fed into a separate multiplexer. The output of this multiplexer is controlled by the operator, or, automatically, by the Digital Signal Processor. Alternatively, the ECG obtained from an external ECG monitor can be used as the reference ECG 62.

The Processing Unit 80 separates the quasi-constant base impedance, $Z_0$, from the time-varying, cardiogenic change, $\Delta Z(t)$, or, if the admittance approach is used, the quasi-constant base admittance, $Y_0$, from the time-varying, cardiogenic change, $\Delta Y(t)$. Details of the subsequent processing applied are described below with respect to FIGS. 9 and 10.

The Processing Unit 80 in FIG. 1 is divided into a Digital Signal Processor 40 and a Microprocessor 66. Here, the microprocessor 66 establishes the interface between the Digital Signal processor 40 and an operator. The functions described as being part of the Digital Signal Processor are not limited to the implementation in the Digital Signal Processor exclusively but may be implemented in the Microprocessor, or vice versa. Alternatively, the Processing Unit may consist of either a Digital Signal Processor or a Microprocessor.

The subject's weight, and other data, is entered via a keyboard 68. Alternatively, data is entered via a touch-screen 70, or via a digital interface 72.

The stroke volume (SV) is calculated by the Processor Unit 80 according to the preferred formula $$SV = V_{EFF} \cdot \sqrt{\frac{\left|\left(\frac{dZ(t)}{dt}\right)_{MIN}\right|}{Z_0}} \cdot FT_C \qquad (1)$$

wherein $$FT_C = \frac{T_{LVE}}{\sqrt{T_{RR}}},$$

and wherein the parameters used for this calculation are those which have been input via the keyboard 68, the touch-screen 70, the digital interface 72 or those which have been determined in the Processing Unit 80 as set out below with respect to FIGS. 6–10. The calculated stroke volume, in conjunction with related cardiovascular parameters, is then displayed on a numerical or graphical screen 70. Alternatively, or in addition, it is transmitted via the data interface 72.

The employment of a separate AC source for each tetrapolar electrode array allows measurement of the skin-electrode impedance, and, thus, monitoring of the skin-electrode contacts of the current electrodes related to this electrode array. The apparatus according to FIG. 1 has the capability to monitor skin-electrode contacts of the left and right hemithorax individually. Qualitatively, a comparator circuit (not shown) can determine whether or not the AC source is overloaded because, for example, of an infinite load (break of connection, loose electrode). Quantitatively, a voltmeter can be connected, or temporally switched, to the outputs of the AC source. The voltmeter measures the voltage across the skin-electrode interfaces and the thorax. The impedance recognized by the AC source is determined as the ratio of the voltage measured and the known AC current applied.

Figure 2:
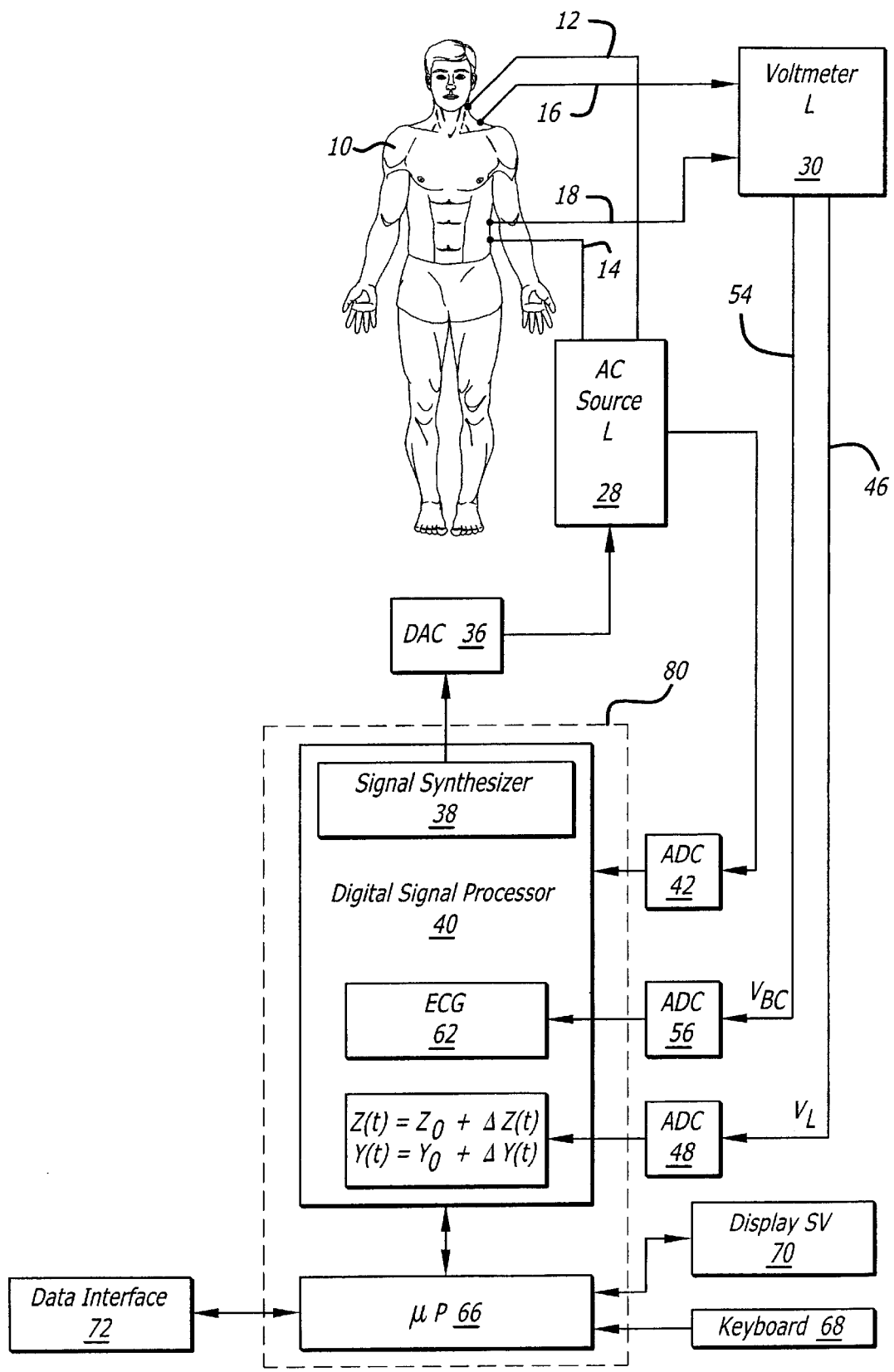
FIG. 2 is a schematic diagram depicting the apparatus of FIG. 1, but limiting the measurement to the left side of the subject's thorax only.

FIG. 2 schematically shows an alternative embodiment of the apparatus according to the present invention. This embodiment is identical with the apparatus as described with respect to FIG. 1, but with the exception that only a single AC source 28, a single Voltmeter 30 and a single tetrapolar surface electrode array are employed. AC Source L 28 is connected to the current electrodes 12 and 14, and Voltmeter L 30, connected to the sensing electrodes 16 and 18. By employing a single electrode array alone (in FIG. 2 the left-sided electrode array), the surface ECG vector $V_{BC}$ 54 is available.

Figure 3:
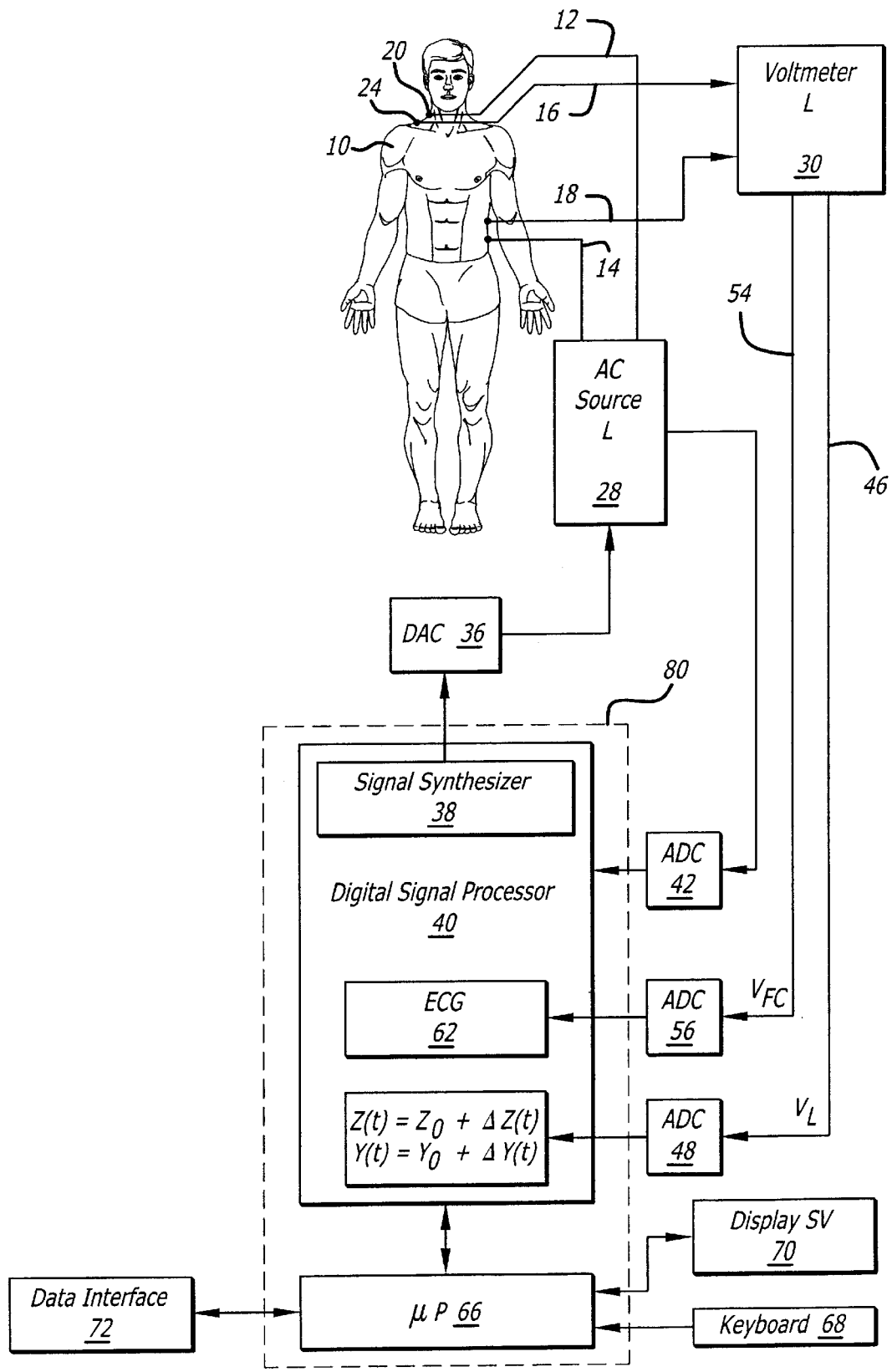
FIG. 3 is a schematic diagram depicting the apparatus of FIG. 2, using a tetrapolar surface electrode array across the subject's thorax.

FIG. 3 schematically shows a further embodiment of the apparatus according to the present invention. This embodiment is identical with the apparatus described with respect to FIG. 2, but with the exception that the tetrapolar electrode array is applied across the thorax. AC Source L 30 is connected to the current electrodes 20 and 14, and Voltmeter L 30, connected to the sensing electrodes 24 and 18. By employment of the cross-thoracic electrode array alone, the surface ECG vector $V_{FC}$ 54 is available.

Figure 4:
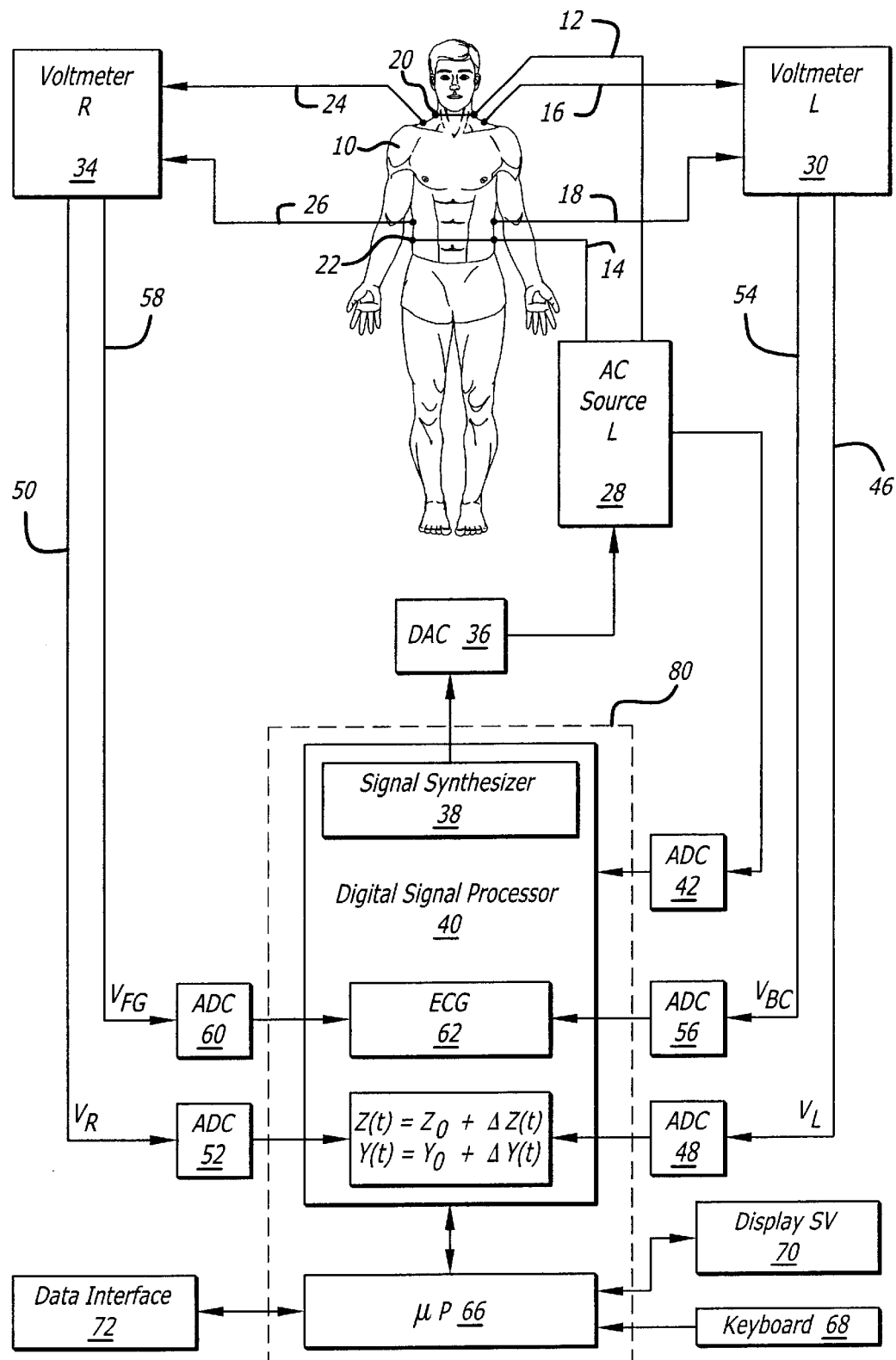
FIG. 4 is a schematic diagram depicting the apparatus of FIG. 1, but utilizing a common AC source for left and right side of the subject's thorax.

FIG. 4 schematically shows an alternative embodiment of the apparatus according to the present invention. This embodiment is identical with the apparatus described with respect to FIG. 1, but with the exception that only one AC source, AC Source L 28, is employed, and interfaced, in parallel, to the current electrodes 12, 14 of the left sided and to the current electrodes right sided electrode array, 20, 22. The capability of the apparatus as shown in FIG. 4 to monitor skin-electrode contact for the current electrodes for left and right sides individually, is compromised, with respect to FIG. 1.

Figure 5:
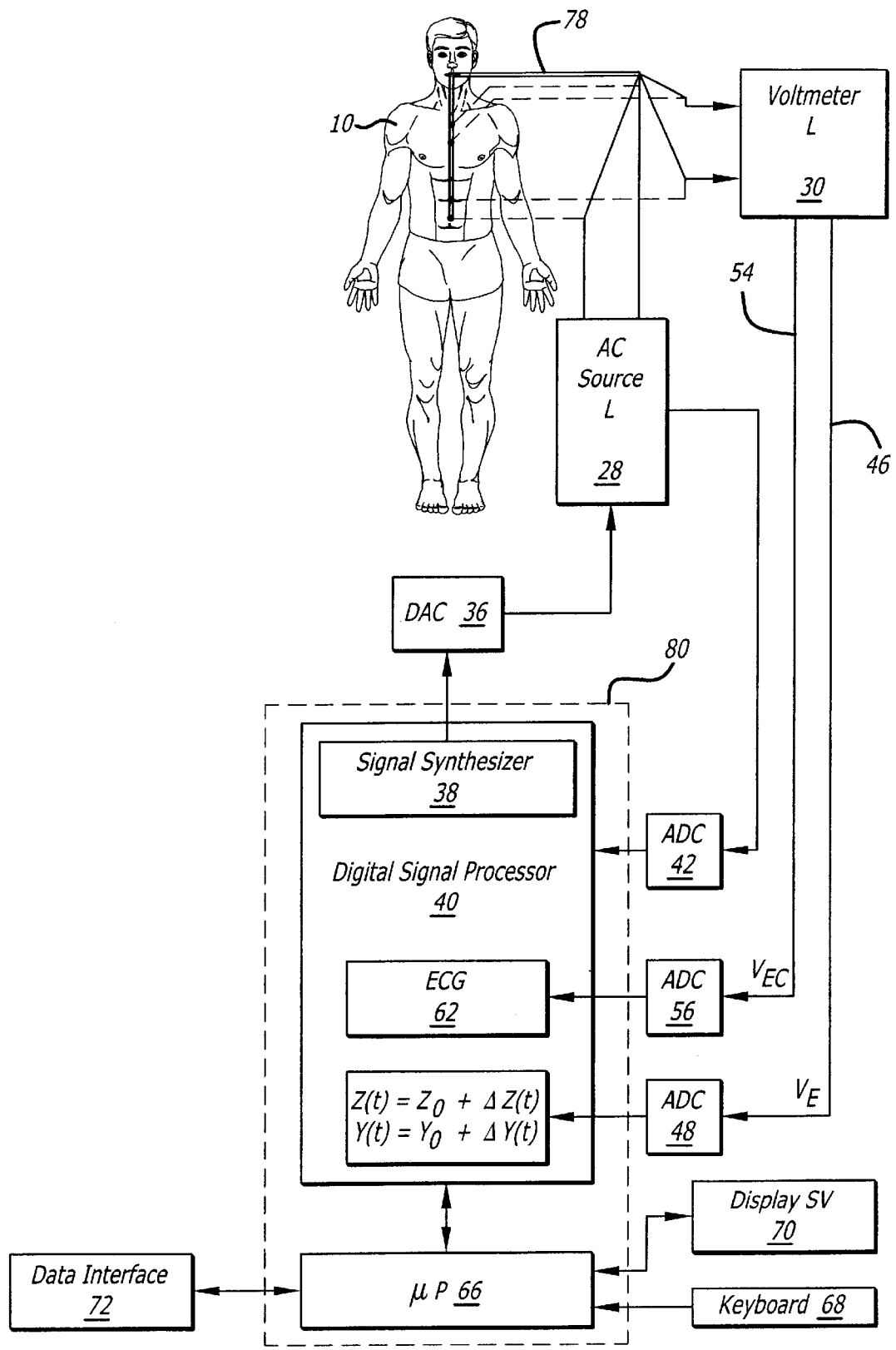
FIG. 5 is a schematic diagram illustrating the application of an esophageal catheter/probe for determining SV by measurement of esophageal electrical bioimpedance (or bioadmittance).

Though the above description was related to the measurement of the impedance (or admittance) of the patient's thorax utilizing surface electrodes, the apparatus and method according to the invention are not restricted to this application. In particular, it is also possible to insert electrodes located on a catheter/probe into the esophagus of a patient. FIG. 5 schematically shows a further embodiment of the apparatus according to the present invention. This apparatus is identical to the apparatus as described with respect to FIG. 2, but utilizing a tetrapolar electrode array located on an esophageal catheter/probe. AC Source L 28 is connected to the current electrodes, and Voltmeter L 30 is connected to the sensing electrodes. The esophageal ECG vector $V_{ES}$ and the esophageal impedance signal $V_E$ are obtained from the voltage sensing electrodes. The impedance (or admittance) changes as a result of the pulsatile vessel flow can be measured.

If the apparatus shown in FIG. 5 is used, principally, the stroke volume can be calculated according to formula (1) given above, wherein coefficients and exponents, and the given implementation of $mZ_T$ as described below have to be adapted. The use of electrodes inserted into the esophagus is, for example, disclosed in U.S. Pat. No. 4,836,214, which is incorporated herein by reference.

In the following, it is described how the various parameters used in formula (1) above are obtained.

Figure 6:
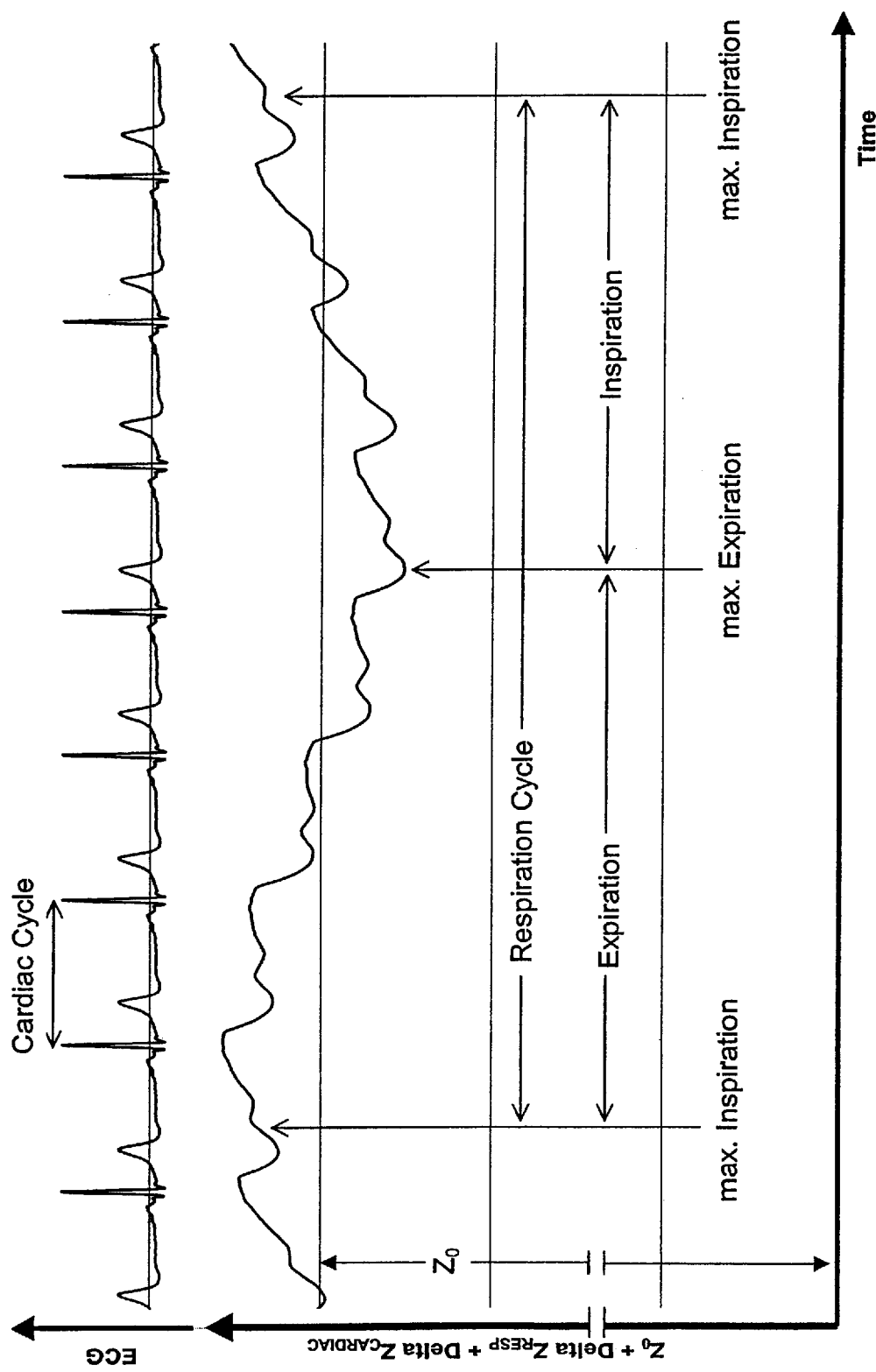
FIG. 6 is a diagram showing the variation of thoracic impedance with a ventilation cycle and with each heart beat.

FIG. 6 illustrates the variation of thoracic impedance with a ventilation cycle and with each heart beat. The electrocardiogram (ECG) on top is a reference for the impedance changes related to the cardiac cycle. The major part of thoracic impedance, the base impedance, $Z_0$, is obtained as the moving average of measured thoracic impedance over a period of, for example, 5 seconds. In a normal healthy subject, $Z_0$ is approximately 30Ω, and does not change from beat to beat. Superimposed on $Z_0$ are changes in impedance ($\Delta Z$) corresponding to both respiration ($\Delta Z_{RESP}$) and pulsatile blood flow ($\Delta Z_{CARD}$). The total thoracic impedance at any time thus equals:

$$Z(t)=Z_0+\Delta Z(t)=Z_0+\Delta Z_{RESP}(t)+\Delta Z_{CARDIAC}(t).$$

In FIG. 6, the respiration cycle begins with maximal inspiration, where air in the lungs causes an increase in thoracic impedance, compared to the base impedance, $Z_0$. During expiration, the ratio of air to liquid in the thorax decreases, as does the thoracic impedance.

Figure 7:
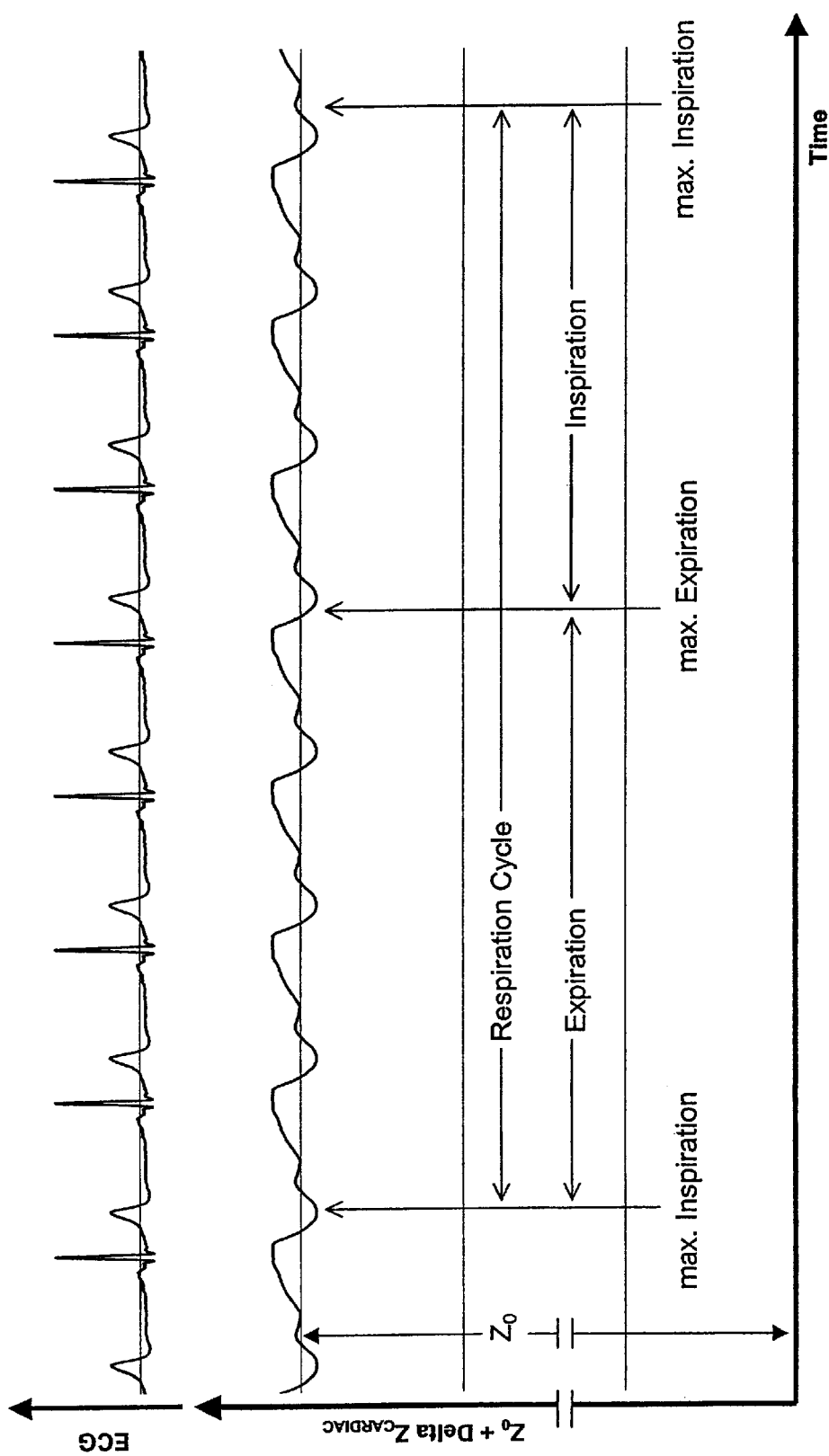
FIG. 7 is a diagram showing the variation of thoracic impedance with each heart beat when ventilation is suppressed.

If respiration is suppressed, or the corresponding effect on the impedance (or admittance) signal is filtered out, only the cardiac-induced pulsatile impedance component, $\Delta Z_{CARDIAC}$, remains (FIG. 7). For simplicity, in the following, $\Delta Z$ is referred to the cardiac-induced impedance change, that is, the impedance change due to ventricular ejection, $\Delta Z_{CARDIAC}$.

Figure 8:
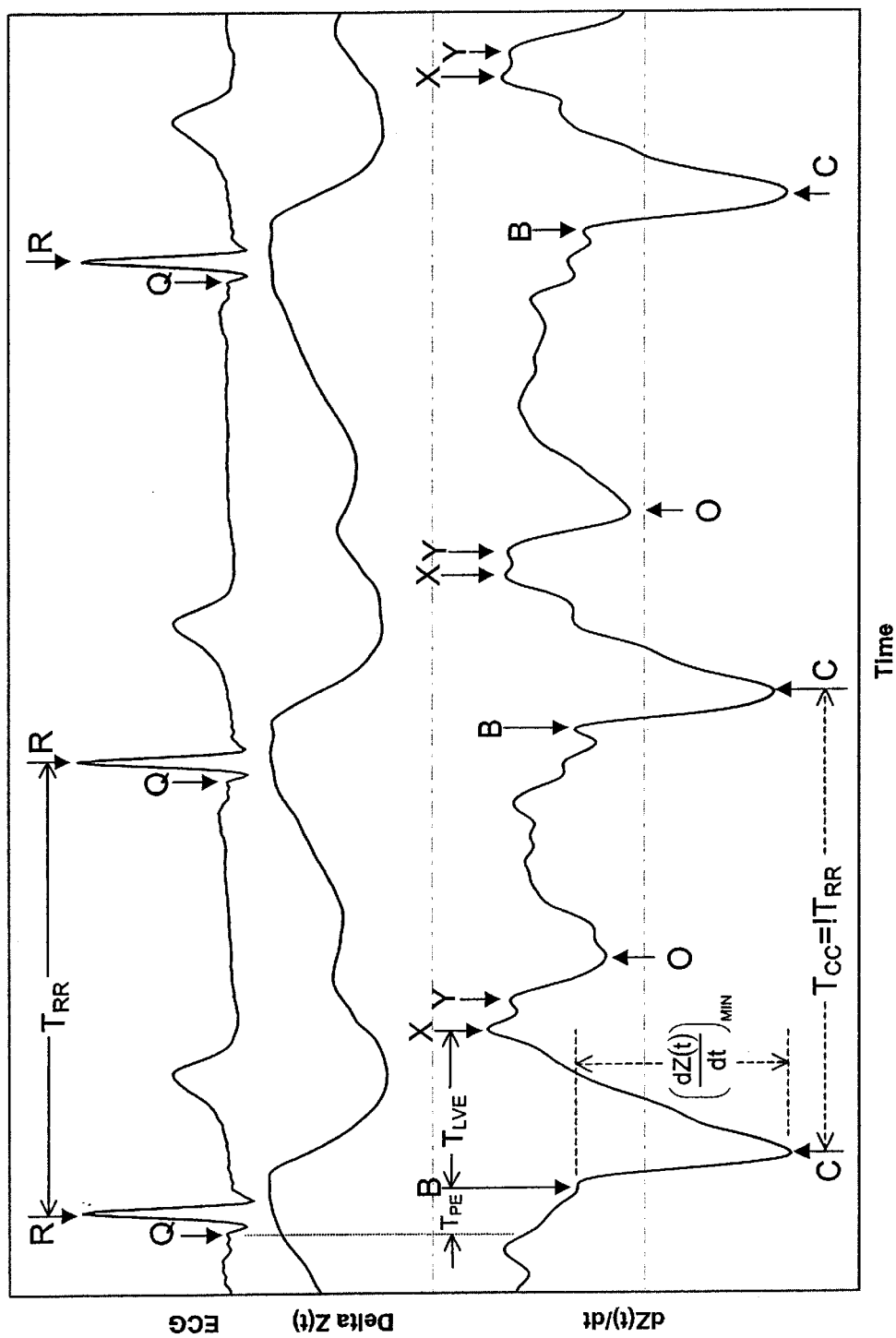
FIG. 8 is a diagram showing curves representing a surface electrocardiogram, the time-varying portion of the cardiogenic thoracic electrical impedance, $\Delta Z(t)$, and the time-derivative of this varying portion of the impedance, $dZ(t)/dt$.

FIG. 8 contains parallel tracings of a scalar surface electrocardiogram (ECG) 100, the thoracic cardiogenic impedance pulse, $\Delta Z(t)$ 102, and the rate of change of thoracic impedance, $dZ(t)/dt$ 104.

The sequential, nearly synchronous, electrical depolarization of the atrial and ventricular heart muscle chambers can be electrically sensed and displayed, and the electrical waveform is characterized, by accepted convention, as the 'PQRST' complex within the ECG tracing. The 'PQRST' complex includes the P-wave, corresponding to the atrial depolarization wave, the Q-wave (labeled 'Q'), corresponding to depolarization of the inter-ventricular septum, the R-wave (labeled 'R'), corresponding to ventricular chamber muscle depolarization, and the T-wave, which represents the repolarization of the ventricular myocardial cells.

The R wave is determined, for example, by continuously obtaining the ECG signal amplitude and, by processing its first time-derivative, its slope. In the event that the absolute slope of the ECG signal exceeds a certain threshold, the ECG Processor 62 establishes a time window, within which the detected absolute peak of the ECG signal represents the temporal occurrence of the R wave.

The time interval between two consecutive R waves is defined as the R-R interval ($T_{RR}$, FIG. 8). In the apparatus according to the preferred embodiment, the R-R interval represents the cardiac cycle period. However, alternatively, other intervals such as, for example, the Q-Q interval can be used to determine the cardiac cycle period within the scope of the invention.

The R wave peak magnitude of each 'PQRST' complex serves as the temporal reference for the processing of $\Delta Z(t)$ and $dZ(t)/dt$. The point Q precedes the peak R wave by approximately 50 ms and is referred to as the onset of electromechanical systole. The time interval between point Q and the opening of aortic valve (point labeled 'B') is known as the pre-ejection period, $T_{PE}$. The time interval between point B and the closure of the aortic valve (point labeled 'X') is defined as left-ventricular ejection time, $T_{LVE}$. The point labeled 'C' indicates the maximal rate of decrease of impedance, i.e. a minimum of $dZ(t)/dt$. The nadir of $dZ(t)/dt$ at this point in time is further referred to as $$\left(\frac{dZ(t)}{dt}\right)_{MIN}.$$

The point labeled 'Y' represents the temporal occurrence of pulmonic valve closure. The point labeled 'O' occurs in diastole and is known to correspond to the early phase of rapid ventricular filling.

The value of $T_{LVE}$ can be automatically determined by a computer analysis in which predetermined criteria are used. The criterion for the determination of point B is the steep decrease of $dZ(t)/dt$ afterwards, whereas point X is the first peak of $dZ(t)/dt$ following $$\left(\frac{dZ(t)}{dt}\right)_{MIN}.$$

Figure 9:
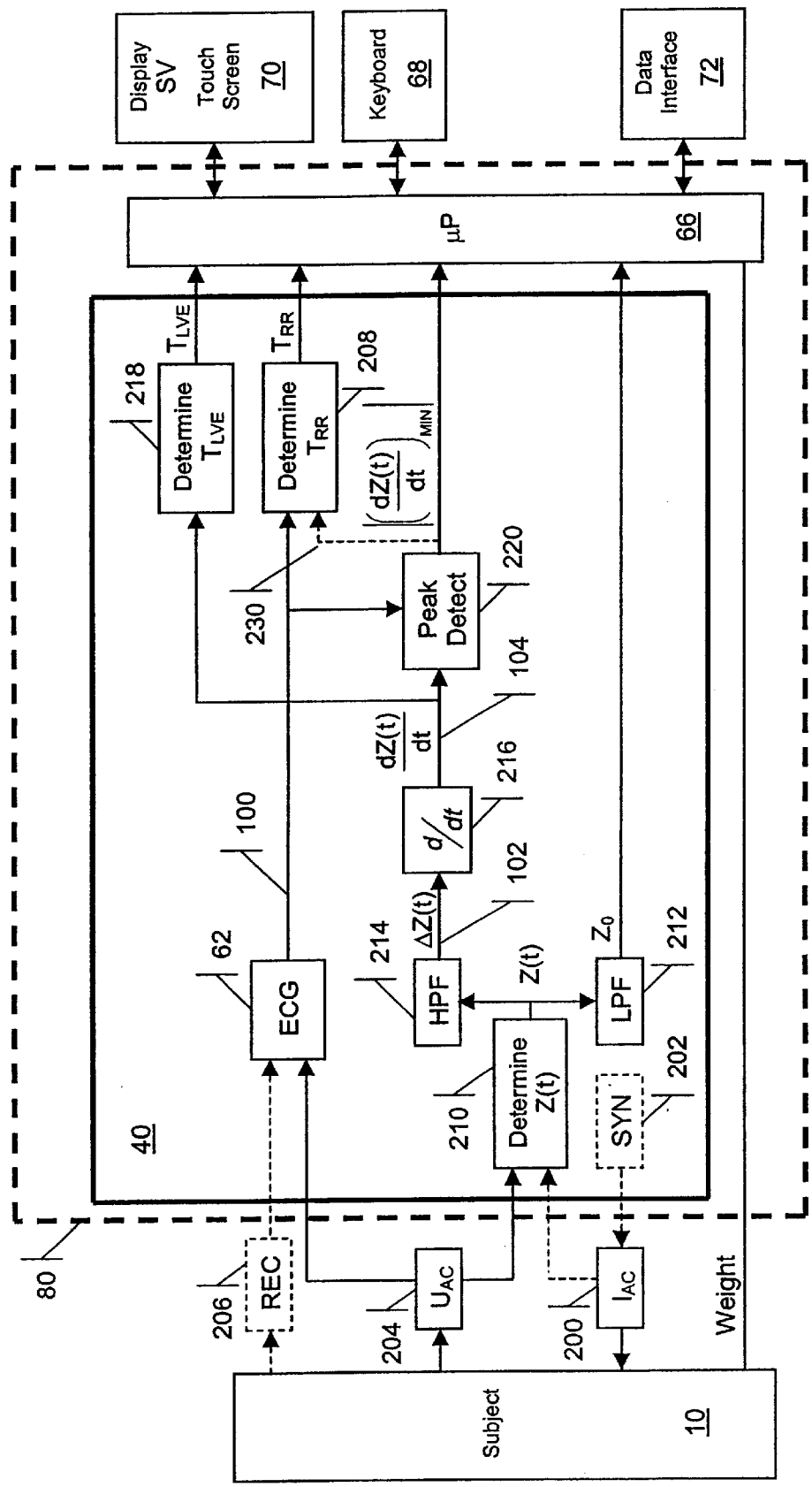
FIG. 9 is a block diagram of the apparatus of the present invention with details of the different components of the apparatus.

The determination of these two points of interest is, hence, easy to perform by someone skilled in the computer art. The latter automatic method is illustrated in FIG. 9 by the means for determining $T_{LVE}$ 218 as part of the Processing Unit (80) and, more specifically, of the Signal Processor (40). Alternatively, the value of $T_{LVE}$ can be determined manually by the operator and then, via the keyboard 68, entered into computation.

The block diagram of FIG. 9 illustrates the acquisition of the ECG and the thoracic impedance Z(t), with emphasis, in particular, on the Digital Signal Processor (DSP) 40 as part of the Processing Unit 80 (indicated by dashed lines). The human subject 10 is shown schematically. The voltage controlled AC source 200 applies an alternating current $I_{AC}$ to the subject's thorax. The voltage controlling the current source is generated externally to the Processing Unit, or by a synthesizer 202 integrated into the Processing Unit (indicated by dashed line from 202 to 200). In the preferred embodiment, the AC source provides a current of constant magnitude, independent of load within reasonable limits. Then the AC magnitude must be made known to the Processing Unit 80. In the event that the magnitude of the AC source is not constant, it must be measured and recognized by the Processing Unit, as indicated by the dashed arrow from 200 to 210.

Because of $I_{AC}$ applied to the thorax, a voltmeter 204 can measure the voltage $U_{AC}$. This voltage contains the signal proportional the applied AC and the (unknown) thoracic impedance carrier signal, modulated on a carrier frequency, and the ECG signal obtained between the sensing electrodes. Within the voltmeter 204, filters are utilized to separate the ECG signal from the applied AC related signal.

The ECG signal is the input to an ECG unit 62, which determines the ECG signal used for temporal reference for the impedance processing. Alternatively, or in addition, the ECG can be recorded and processed by a source 206 separate and external to the apparatus described herein (indicated by dashed arrows from 10 via 206 to 62). An apparatus 208 determines the RR interval, $T_{RR}$, from the reference ECG 100 (see also FIG. 6) provided by the ECG processing unit 62. Alternatively, $T_{RR}$ can be determined as the time interval between two consecutive occurrences of $$\left|\left(\frac{dZ(t)}{dt}\right)_{MIN}\right|,$$

which approximates $T_{RR}$ (indicated in FIG. 8 and, by a dashed line at 230, in FIG. 9). In an alternative embodiment of the invention, the units 62 and 208 are not part of the processing unit 80 but are external devices.

The voltmeter 204 eliminates, by demodulation, the AC carrier frequency from the portion of $U_{AC}$ corresponding to the applied AC. The apparatus 210 determines the impedance Z(t) by calculating the ratio of voltage obtained and alternating current $I_{AC}$ applied:

$$Z(t) = \frac{U(t)}{I(t)}.$$

A low-pass filter (LPF) 212 is applied to Z(t) in order to obtain the base impedance, $Z_0$. A high-pass filter (HPF) 214 is applied to Z(t) in order to obtain the thoracic cardiogenic impedance pulse, $\Delta Z(t)$ 102 (see also FIG. 6). The purpose of the high-pass filter is also to eliminate impedance changes due to pulmonary ventilation (respiration). A differentiator 216 determines the first time-derivative, or slope of $\Delta Z(t)$, that is, dZ(t)/dt. It is also referred to as the rate of change of thoracic impedance 104 (see also FIG. 6).

With reference to FIG. 6: The dZ(t)/dt signal 104 exhibits characteristic landmarks, as described. The left-ventricular ejection time $T_{LVE}$ is determined from the dZ(t)/dt signal. Applying basic curve mathematical discussion, one skilled in the art can identify the temporal occurrence of aortic valve opening, point B (see arrow), as the "notch" just before the steep down-slope of dZ(t)/dt (after the R wave, but prior the point C). Aortic valve closure, labeled as point X and pointed to with an arrow, corresponds to a dZ(t)/dt peak after point C. The digital signal processor (DSP) 40 obtains these points B, C and X, automatically from a processing unit 218 (FIG. 7). This unit determines $T_{LVE}$ as the time interval between point B and point X.

Turning back to FIG. 9, a peak detector 220 is applied to the dZ(t)/dt signal 104 in order to obtain the peak rate of change of impedance during systole, see point C in FIG. 7, and its occurrence in time. The ECG provided by unit 62 is utilized as a temporal reference. The output of the peak detector, relevant for the SV determination, is the absolute peak rate of change of impedance, $$\left|\left(\frac{dZ(t)}{dt}\right)_{MIN}\right|.$$

The left-ventricular ejection time, $T_{LVE}$, the RR interval, $T_{RR}$, the base impedance, $Z_0$, and the absolute peak rate of change of impedance, $$\left|\left(\frac{dZ(t)}{dt}\right)_{MIN}\right|,$$

are furthermore transferred to the microprocessor ($\mu$P) 66. The $\mu$P 66 determines from the parameters, measured and processed by the DSP 40, and other parameters entered, for example, via the keyboard 68 (specifically: weight) the stroke volume (SV). The display 70 connected with the $\mu$P 66 illustrates the SV and the values of other related cardiodynamic parameters. Alternatively, a touch screen can be implemented instead of a display, enabling the operator to enter weight and other demographic data via the screen. The $\mu$P 66 can receive data obtained by other, external devices, for example, $T_{RR}$ and/or $T_{LVE}$, through a data interface 72, or send data to other, external devices, such as patient monitors.

Figure 10:
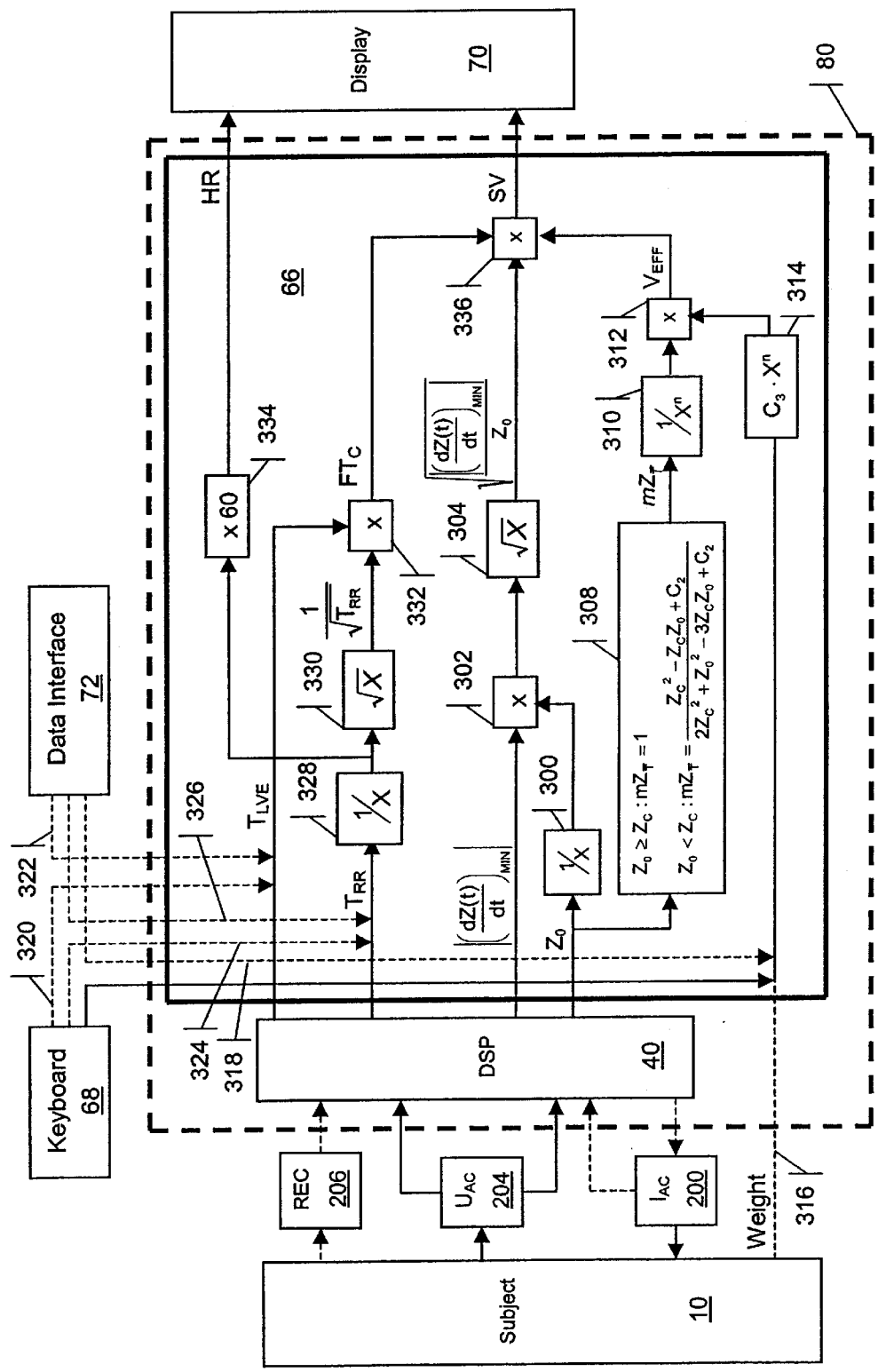
FIG. 10 is the block diagram of FIG. 9 in which the Digital Signal Processor is shown in less detail whereas the Microprocessor is shown in more detail.

The block diagram of FIG. 10 illustrates the acquisition of the ECG and the thoracic impedance Z(t), with emphasis, in particular, on the microprocessor ($\mu$P) 66. The $\mu$P 66 receives the value for $Z_0$ from the DSP 40. A unit 300 calculates the reciprocal of $Z_0$, which is then multiplied 302 with the value of $$\left|\left(\frac{dZ(t)}{dt}\right)_{MIN}\right|$$

received from the DSP. This product is applied to unit 304, which determines the square root. The result equals $$\sqrt{\frac{\left|\left(\frac{dZ(t)}{dt}\right)_{MIN}\right|}{Z_0}},$$

which is an integral input for the SV calculation.

The $\mu$P utilizes the value for $Z_0$ to determine the index of transthoracic specific impedance 308, further referred to as $mZ_T$. This index reflects the presence or absence of abnormal lung water, and is within the scope of the invention. $mZ_T$ relates to the magnitude or degree of abnormal shunting or bypassing of applied AC around the $V_{EFF}$, via additional abnormal conductive pathways. The critical level of base impedance is defined as $Z_C$, where $Z_C$ is greater than 15$\Omega$ and less than 25$\Omega$, i.e. 15$\Omega$<Zc<25$\Omega$. In the preferred embodiment, $Z_C$=20$\Omega$ (Critchley L A H et al. The effect of lung injury and excessive lung fluid on impedance cardiac output measurements in the critically ill. Intensive Care Med 2000; 26: 679–685; Critchley L A H et al. Lung fluid and impedance cardiography. Anesthesia 1998; 53: 369–372;

Shoemaker W C et al. Multicenter study of noninvasive systems as alternatives to invasive monitoring of acutely ill emergency patients. Chest 1998; 114: 1643–1652; Shoemaker W C et al. Multicenter trial of a new thoracic electrical bioimpedance device for cardiac output estimation. Crit Care Med 1994; 22: 1907–1912).

In the normal cardiopulmonary state, indicated by $Z_0 \geq Z_C$, $mZ_T$ equals 1. In the abnormal cardiopulmonary state, i.e. in the presence of excess thoracic liquids ($Z_0 < Z_C$), $mZ_T$ is less than 1 and greater than 0, i.e. $0 < mZ_T < 1$, and is calculated accordingly:

$$mZ_T = \frac{Z_C^2 - Z_C Z_0 + C_2}{2Z_C^2 + Z_0^2 - 3Z_C Z_0 + C_2}.$$

$C_2$ is a constant and, in the preferred embodiment, taken to 0. In a simplified version of the invention, $mZ_T$ is taken to be 1 for all values of $Z_0$.

A unit 310 calculates the reciprocal value of $mZ_T$, or a power of it. The output of 310 is multiplied in unit 312 with the output of a unit 314 that calculates the mass-based volumetric equivalent of thoracic blood volume in the stable, normal cardiopulmonary state. Unit 314 requires the input of the weight of the subject 10 under investigation (indicated by the dashed line at 316). In the preferred embodiment, weight is entered via the keyboard 68 or the touch screen 70. Alternatively, the value for weight is entered elsewhere and received via a data interface 72 (indicated by dashed line at 318). The output of the multiplier 312 is $V_{EFF}$, with $$V_{EFF} = \frac{C_3 \cdot W^X}{mZ_T^N},$$

where $C_3$ is taken to be 13, but can alternatively have any other value in a range of 0,01–15. In the case of the embodiments shown in FIGS. 1–4, $C_3$ is preferably comprised in the range of 11–15. In the case of the embodiment shown in FIG. 5, $C_3$ is preferably comprised in the range of 0.01–2.00. In the preferred embodiment, the exponent for weight, X, is taken to be 1.025. with its limits otherwise being 0.9–1.1, which are extrapolated from data presented in the article by Holt et al. with the title "Ventricular volumes and body weight in mammals", Am.J.Physiol. 1968; 215:704–715. In the preferred embodiment, the exponent for $mZ_T$, N, is taken to be 1.5, with its limits otherwise being 1.0–2.0.

$V_{EFF}$ is, according to the model used here, the mass-based volumetric equivalent of the thoracic blood volume in the stable, normal state. $V_{EFF}$ also represents the total thoracic liquids in unstable cardiopulmonary disease states. These conditions are characterized by the abnormal presence of excess thoracic liquids. In the articles by Critchley et al. (Lung fluid and impedance cardiography. Anesthesia 1998; 53: 369–372; The effect of lung injury and excessive lung fluid on impedance cardiac output measurements in the critically ill. Intensive Care Med 2000; 26: 679–685) and Shoemaker et al. (Multicenter trial of a new thoracic electrical bioimpedance device for cardiac output estimation. Crit Care Med 1994; 22: 1907–1912; Multicenter study of noninvasive systems as alternatives to invasive monitoring of acutely ill emergency patients. Chest 1998; 114: 1643–1652) the impact of excess thoracic liquids related to SV determination by means of electrical bioimpedance have been observed.

The volume $V_{EFF}$, determined as $$V_{EFF} = \frac{C_3 \cdot W^X}{mZ_T^N},$$

is an integral part of the preferred embodiment and the new SV equation proposed within. With proper scaling, other volumes such as, for example, the ones defined by Sramek and Bernstein, based on weight deviation from ideal weight and height, can be used instead. Employment of other volumes is at the expense of accuracy over a wide spectrum of subjects, because of their body habita and disease states.

The DSP 40 provides the measured values for the left-ventricular ejection time, $T_{LVE}$, and the RR interval, $T_{RR}$. Alternatively, $T_{LVE}$ can be manually entered via the keyboard 68 (indicated by dashed line at 320), or measured, or entered elsewhere and transmitted via a data interface 72 (indicated by dashed line at 322).

Alternatively, $T_{RR}$ can be manually entered via a keyboard 68 (indicated by dashed line at 324), or measured, or entered elsewhere and transmitted via a data interface 72 (indicated by dashed line at 326). Unit 328 determines the reciprocal value of $T_{RR}$, which equals the human circulatory system frequency:

$$f_0 = \frac{1}{T_{RR}}.$$

The circulatory frequency, $f_0$, or its reciprocal, $T_{RR}$, can be averaged for a plurality of periods. For example, these values can be averaged over the previous ten cardiac cycles ("moving average").

Alternatively, the circulatory frequency, $f_0$, can be entered manually by the operator trough the keyboard 68, or transmitted via a data interface 72.

The value for heart rate (HR, in beats per minute) is calculated by multiplying 334 the circulatory system $f_0$ with 60.

Alternatively, the heart rate, HR, can be entered manually by the operator trough the keyboard 68, or transmitted via a data interface 72.

Unit 330 determines the square root. The output of unit 330 is the Bazett transformation (Bazett M C. An analysis of the time relations of electrocardiograms. Heart 1920, 7: 353–364), which, when multiplied in unit 332 with $T_{LVE}$, normalizes $T_{LVE}$ for system mechanical frequency. This normalized $T_{LVE}$, also known as corrected flow time, $FT_C$, $$FT_C = \frac{T_{LVE}}{\sqrt{T_{RR}}},$$

is an integral part of the preferred embodiment and the new SV equation proposed therewith. Other embodiments may use $T_{LVE}$ instead of $FT_C$ for the SV calculation, at the expense of accuracy at higher heart rates.

A multiplier 336 calculates the product of $V_{EFF}$, $$\sqrt{\frac{\left|\left(\frac{dZ(t)}{dt}\right)_{MIN}\right|}{Z_0}}$$

and $FT_C$, which equals the SV approximated by the apparatus ([SV]=mL):

$$SV = V_{EFF} \cdot \sqrt{\frac{\left|\left(\frac{dZ(t)}{dt}\right)_{MIN}\right|}{Z_0}} \cdot FT_C = V_{EFF} \cdot \sqrt{\frac{\left|\left(\frac{dZ(t)}{dt}\right)_{MIN}\right|}{Z_0}} \cdot \frac{T_{LVE}}{\sqrt{T_{RR}}}$$

The value of SV is displayed on a numerical or graphical screen 70. Alternatively, or in addition, it can also be transmitted to a data interface 72.

Cardiac output [L/min] is then calculated from SV [mL] as $$CO = \frac{SV}{T_{RR}} \cdot \frac{60}{1000}.$$

The measured values can be averaged over a plurality of periods. For example, these values can be averaged over the previous ten cardiac cycles ("moving average").

Although FIGS. 1–5 and 7–8 indicate that the majority of the functional units are implemented into a Processing unit, namely a signal processor and a microprocessor, part or all of the functions can be arranged as individual circuitries.

Furthermore, the approximation of SV according to this invention is not limited to the impedance method, but can be performed using the admittance approach. With $$Y(t) = \frac{1}{Z(t)},$$

$$T_0 = \frac{1}{Z_0}$$

and $$\left(\frac{dY(t)}{dt}\right)_{MAX} \cong \frac{1}{Z_0^2} \cdot \left|\left(\frac{dZ(t)}{dt}\right)_{MIN}\right|,$$

the SV is approximated according to $$SV = V_{EFF} \cdot \sqrt{\frac{\left|\left(\frac{dY(t)}{dt}\right)_{MAX}\right|}{Y_0}} \cdot FT_C.$$

With respect to the admittance approach, $V_{EFF}$ is determined by $$V_{EFF} = C_3 \cdot W^X \cdot mY_T^N,$$

where $C_3$ is taken to be 13, but can alternatively have any other value in a range of 0.01–15. In the preferred embodiment, the exponent for weight, X, is taken to be 1.025, with its limits otherwise being 0.9–1.1. In the preferred embodiment, the exponent for $mY_T$, N, is taken to be 1.5, with its limits otherwise being 1.0–2.0.

The value for $Y_0$ is utilized to determine the index of transthoracic specific admittance, or conductivity, further referred to as $mY_T$. This index reflects the presence or absence of abnormal lung water, and is within the scope of the invention. $mY_T$ relates to the magnitude or degree of abnormal shunting or bypassing of applied AC around the $V_{EFF}$, via additional abnormal conductive pathways. The critical level of base admittance is defined as $Y_C$, where $Y_C$ is greater than 0.04 $\Omega^{-1}$ (corresponding to 25Ω) and less than 0.0667 $\Omega^{-1}$ (corresponding to 15Ω), i.e. 0.04 $\Omega^{-1} < Y_C < 0.0667$ $\Omega^{-1}$. In the preferred embodiment, $Y_C = 0.05$ $\Omega^{-1}$ (corresponding to 20Ω).

In the normal cardiopulmonary state, indicated by $Y_0 \leq Y_C$, $mY_T$ equals 1. In the abnormal cardiopulmonary state, i.e. in the presence of excess thoracic liquids ($Y_0 > Y_C$), $mY_T$ is greater than 1, i.e. $mY_T > 1$, and is calculated accordingly:

$$mY_T = \frac{2Y_0^2 + Y_C^2 - 3Y_C Y_0 + C_2}{Y_0^2 - Y_C Y_0 + C_2}.$$

$C_2$ is a constant and, in the preferred embodiment, taken to 0. In a simplified version of the invention, $mY_T$ is taken to be 1 for all values of $Y_0$.

It is noted that, when electrical admittance is determined, instead of electrical impedance, the processing performed by the DSP 40 is similar. In this case, the DSP obtains the base admittance, $Y_0$, after applying a low-pass filter to $Y(t)$, which is the ratio of $I_{AC}$ 200 to $U_{AC}$ 204:

$$Y(t) = \frac{I(t)}{U(t)}.$$

The application of a high-pass filter to $\Delta Y(t)$ and a differentiator reveals the rate of change of cardiogenic admittance, $dY(t)/dt$. In fact, the $dY(t)/dt$ signal appears, in approximation, as an inverted $dZ(t)/dt$ waveform. In the case of the admittance approach, the peak detector determines the peak rate of change of admittance, $$\left(\frac{dY(t)}{dt}\right)_{MAX}.$$

Other modifications and variations will become apparent to those skilled in the art in view of the above descriptions. The present invention is hence not limited to the preferred embodiment described above, but is only limited by the following claims.

What is claimed is:

1. An apparatus for determining an approximate value for a stroke volume SV (in milliliter) of a subject's heart, comprising
   a) means for measuring an electrical impedance Z(t) of a part of the subject's body, wherein a value of said electrical impedance Z(t) changes with time t as a consequence of the beating of the heart;
   b) means for determining a base impedance $Z_0$ as a part of said electrical impedance Z(t) which does not change significantly during a period of one cardiac cycle;
   c) means for determining a peak magnitude $$\left|\left(\frac{dZ(t)}{dt}\right)_{MIN}\right|$$

of a temporal derivative $$\frac{dZ(t)}{dt}$$

of said electrical impedance Z(t), indicating an absolute maximum rate of change of said electrical impedance Z(t) during a systolic period of the cardiac cycle;
   d) means for determining a left ventricular ejection time, $T_{LVE}$;
   e) means for determining the cardiac cycle period $T_{RR}$ of the heart; and f) means for calculating said approximate value of the stroke volume SV wherein said calculating means is adapted to evaluate a formula $$SV = V_{EFF} \cdot C_1 \cdot \left( \frac{\left|\left(\frac{dZ(t)}{dt}\right)_{MIN}\right|}{Z_0} \right)^n \cdot \left(\frac{1}{T_{RR}}\right)^m \cdot T_{LVE}$$

wherein $0.15 \leq n \leq 0.8$ and $0 \leq m \leq 1.5$,
and wherein $V_{EFF}$ is an approximate value of the subject's volume of electrically participating tissue, and wherein $C_1$ is a constant.

2. The apparatus of claim 1, wherein m is non-zero.
3. The apparatus of claim 1, wherein $0.3 \leq n \leq 0.65$.
4. The apparatus of claim 1, wherein $0.45 \leq n \leq 0.55$.
5. The apparatus of claim 1, wherein $m=1-n$.
6. The apparatus of claim 1, wherein $C_1=1$.
7. The apparatus of claim 5, wherein $m=n=0.5$.
8. The apparatus of claim 1, wherein $$V_{EFF} = \frac{C_3 \cdot W^X}{mZ_T^N}$$

(in milliliter),
wherein W is the subject's weight in kilogram (kg),
wherein $C_3$ is a coefficient with constant value and X and N are exponents with constant values,
wherein $mZ_T=1$ for $Z_0 \geq Z_C$, and $$mZ_T = \frac{Z_C^2 - Z_C Z_0 + C_2}{2Z_C^2 + Z_0^2 - 3Z_C Z_0 + C_2}$$

for $Z_0 < Z_C$, and wherein $Z_C$ is a constant, and wherein $C_2$ is a constant.

9. The apparatus of claim 8, wherein $C_2=0$.
10. The apparatus of claim 8, wherein $C_3$ is a value in the range of 0.01–15.
11. The apparatus of claim 10, wherein $C_3$ is approximately 13.
12. The apparatus of claim 8, wherein X is a value in the range of 0.9–1.1.
13. The apparatus of claim 12, wherein X is approximately 1.025.
14. The apparatus of claim 8, wherein N is a value in the range of 1.0–2.0.
15. The apparatus of claim 14, wherein N is approximately 1.5.
16. The apparatus of claim 8, wherein Zc is a value in the range of 15–25Ω.
17. The apparatus of claim 16, wherein $Z_C$ is approximately 20Ω.
18. The apparatus of claim 1, wherein $V_{EFF}=C_3 \cdot W^X$ (in milliliter), wherein W is the subject's weight in kilogram, and wherein $C_3$ is a coefficient with a constant value and X is an exponent with constant value.
19. The apparatus of claim 18, wherein $C_3$ is a value in the range of 0.01–15.
20. The apparatus of claim 19, wherein $C_3$ is approximately 13.
21. The apparatus of claim 18, wherein X is a value in the range of 0.9–1.1.
22. The apparatus of claim 21, wherein X is approximately 1.025.
23. The apparatus of claim 1, wherein said means for measuring said electrical impedance Z(t) comprises:

at least two pairs of electrodes;
a current source generating an alternating current I(t) of predetermined amplitude;
wherein one pair of electrodes is adapted to be connected to said current source;
means for measuring a voltage U(t) caused by applying said alternating current;
wherein one pair of electrodes is connected to said means for measuring the voltage U(t);
means for determining said electrical impedance Z(t) from the voltage U(t) and the current I(t).

24. The apparatus of claim 1, wherein said means for determining the peak magnitude $$\left|\left(\frac{dZ(t)}{dt}\right)_{MIN}\right|$$

comprises:

means for determining $\Delta Z(t)$ from $Z(t)$;
means for calculating $$\frac{dZ(t)}{dt}$$

for at least the systolic period of one cardiac cycle;
means for determining the maximum of an input function.

25. The apparatus of claim 24, wherein said means for determining $\Delta Z(t)$ is a high-pass filter.
26. The apparatus of claim 1, wherein said means for determining $Z_0$ is a low-pass filter.
27. The apparatus of claim 1, wherein said means for determining $T_{LVE}$ determines $T_{LVE}$ by determining by analysis of $$\frac{dZ(t)}{dt}$$

a point in time when an aortic valve opens;
a point in time when the aortic valve closes; and by calculating a time difference of said closing point in time and said opening point in time.

28. The apparatus of claim 1, wherein said means for determining the cardiac cycle period $T_{RR}$ comprises means for analyzing at least one of a group of Z(t), $\Delta Z(t)$, $$\frac{dZ(t)}{dt}$$

and $$\left|\left(\frac{dZ(t)}{dt}\right)_{MIN}\right|.$$

29. The apparatus of claim 1, wherein said means for determining the cardiac cycle period $T_{RR}$ comprises means for measuring an electrocardiogram and means for analyzing the measured values.
30. The apparatus of claim 1, wherein at least one of said means for determining $$\left|\left(\frac{dZ(t)}{dt}\right)_{MIN}\right|,$$

$Z_0$, $T_{LVE}$ and $T_{RR}$ and said means for calculating are comprised in a processing unit.

31. The apparatus of claim 1, further comprising means for outputting a signal, which is representative of SV.

32. The apparatus of claim 1, further comprising means for visually displaying SV to a user.

33. The apparatus of claim 1, further comprising means for calculating an approximate value for a cardiac output CO of the subject's heart (in liter/minute), wherein said calculating means is adapted to evaluate a formula $$CO = SV \cdot \frac{1}{T_{RR}} \cdot \frac{60}{1000}.$$

34. An apparatus for determining an approximate value for a stroke volume SV of a subject's heart, comprising
 a) a current source outputting an alternating current I(t) of predetermined amplitude to two electrodes;
 b) means for measuring a voltage U(t) caused by said alternating current between two electrodes; and
 c) a processing unit receiving at least a signal representative of U(t), said processing unit being adapted to:
  calculate an impedance Z(t) from the voltage U(t) and a value of the current I(t);
  input Z(t) into a low-pass filter, an output of said low-pass filter being $Z_0$;
  input Z(t) into a high-pass filter, an output of said high-pass filter being $\Delta Z(t)$;
  calculate a peak magnitude $$\left|\left(\frac{dZ(t)}{dt}\right)_{MIN}\right|$$

of $$\frac{dZ(t)}{dt};$$

determine a left ventricular ejection time $T_{LVE}$ from at least one of Z(t), $\Delta Z(t)$ and $$\frac{dZ(t)}{dt}$$

by using predetermined criteria;
determine a cardiac cycle period $T_{RR}$ of the heart from at least one of Z(t), $\Delta Z(t)$ and $$\frac{dZ(t)}{dt}$$

by using predetermined criteria;
calculate SV according to a formula $$SV = V_{EFF} \cdot C_1 \cdot \left(\frac{\left|\left(\frac{dZ(t)}{dt}\right)_{MIN}\right|}{Z_0}\right)^n \cdot \left(\frac{1}{T_{RR}}\right)^m \cdot T_{LVE}$$

wherein $0.15 \leq n \leq 0.8$ and $0 < m < 1.5$,
and wherein $V_{EFF}$ is an approximate value of the subject's volume of electrically participating tissue, and wherein $C_1$ is a constant.

35. The apparatus of claim 34, wherein n=m=0.5, and wherein $C_1=1$.

36. An apparatus for determining an approximate value for the stroke volume SV of a subject's heart, comprising
 a) a current source outputting an alternating current I(t) of predetermined amplitude to two electrodes;
 b) means for measuring a voltage U(t) caused by said alternating current between two electrodes;
 c) means for measuring an electrocardiogram; and
 d) a processing unit receiving at least a signal representative of U(t) and measured values of said electrocardiogram, said processing unit being adapted to:
  calculate an impedance Z(t) from the voltage U(t) and a value of the current I(t);
  input Z(t) into a low-pass filter, an output of said low-pass filter being $Z_0$;
  input Z(t) into a high-pass filter, an output of said high-pass filter being $\Delta Z(t)$;
  calculate a peak magnitude $$\left|\left(\frac{dZ(t)}{dt}\right)_{MIN}\right|$$

of $$\frac{dZ(t)}{dt};$$

determine a left ventricular ejection time $T_{LVE}$ from at least one of Z(t), $\Delta Z(t)$ and $$\frac{dZ(t)}{dt}$$

by using predetermined criteria;
determine a cardiac cycle period $T_{RR}$ of the heart from the measured values of said electrocardiogram;
calculate SV according to a formula $$SV = V_{EFF} \cdot C_1 \cdot \left(\frac{\left|\left(\frac{dZ(t)}{dt}\right)_{MIN}\right|}{Z_0}\right)^n \cdot \left(\frac{1}{T_{RR}}\right)^m \cdot T_{LVE}$$

wherein $0.15 < n < 0.8$ and $0 < m < 1.5$,
and wherein $V_{EFF}$ is an approximate value of the subject's volume of electrically participating tissue, and wherein $C_1$ is a constant.

37. The apparatus of claim 36, wherein n=m=0.5, and wherein $C_1=1$.

38. An apparatus for determining an approximate value for a stroke volume SV of a subject's heart, comprising
 a) a current source outputting an alternating current I(t) of predetermined amplitude to two electrodes;
 b) means for measuring a voltage U(t) caused by said alternating current between two electrodes;
 c) means for measuring an electrocardiogram and means for calculating a cardiac cycle period $T_{RR}$ of the heart from measured values of said electrocardiogram;
 d) a processing unit receiving at least a signal representative of U(t) and a signal representative of $T_{RR}$, said processing unit being adapted to:

calculate an impedance Z(t) from the voltage U(t) and a value of the current I(t);
input Z(t) into a low-pass filter, an output of said low-pass filter being $Z_0$;
input Z(t) into a high-pass filter, an output of said high-pass filter being $\Delta Z(t)$;
calculate a peak magnitude $$\left|\left(\frac{dZ(t)}{dt}\right)_{MIN}\right|$$

of $$\frac{dZ(t)}{dt};$$

determine a left ventricular ejection time $T_{LVE}$ from at least one of Z(t), $\Delta Z(t)$ and $$\frac{dZ(t)}{dt}$$

by using predetermined criteria;
calculate SV according to a formula $$SV = V_{EFF} \cdot C_1 \left(\frac{\left|\left(\frac{dZ(t)}{dt}\right)_{MIN}\right|}{Z_0}\right)^n \cdot \left(\frac{1}{T_{RR}}\right)^m \cdot T_{LVE}$$

wherein $0.15 < n < 0.8$ and $0 < m \leq 1.5$,
and wherein $V_{EFF}$ is an approximate value of the subject's volume of electrically participating tissue, and wherein $C_1$ is a constant.

39. The apparatus of claim 38, wherein said means for calculating the cardiac cycle period $T_{RR}$ is adapted to output a signal representative of $T_{RR}$ to the processing unit.

40. The apparatus of claim 38 wherein n=m=0.5, and wherein $C_1=1$.

41. An apparatus for determining an approximate value for a stroke volume SV of a subject's heart, comprising
   a) a current source outputting an alternating current I(t) of predetermined amplitude to two electrodes;
   b) means for measuring a voltage U(t) caused by said alternating current between two electrodes;
   c) a processor unit receiving at least a signal representative of U(t), said processing unit being adapted to:
      calculate an impedance Z(t) from the voltage U(t) and a value of the current I(t);
      input Z(t) into a low-pass filter, an output of said low-pass filter being $Z_0$;
      input Z(t) into a high-pass filter, an output of said high-pass filter being $\Delta Z(t)$;
      calculate a peak magnitude $$\left|\left(\frac{dZ(t)}{dt}\right)_{MIN}\right|$$

of $$\frac{dZ(t)}{dt};$$

determine a left ventricular ejection time $T_{LVE}$ from at least one of Z(t), $\Delta Z(t)$ and $$\frac{dZ(t)}{dt}$$

by using predetermined criteria;
calculate SV according to a formula $$SV = V_{EFF} \cdot C_1 \cdot \left(\frac{\left|\left(\frac{dZ(t)}{dt}\right)_{MIN}\right|}{Z_0}\right)^n \cdot T_{LVE}$$

wherein $0.15 < n < 0.8$,
and wherein $V_{EFF}$ is an approximate value of the subject's volume of electrically participating tissue, and wherein $C_1$ is a constant.

42. A method of determining an approximate value for a stroke volume SV of a subject's heart, comprising the steps of:
   a) measuring an impedance Z(t) of a part of the subject's body, wherein a value of said impedance Z(t) changes with time t as a consequence of the beating of the heart;
   b) determining a mean impedance $Z_0$;
   c) determining a peak magnitude $$\left|\left(\frac{dZ(t)}{dt}\right)_{MIN}\right|$$

of a derivative $$\frac{dZ(t)}{dt}$$

of said impedance Z(t) over the time t by using the measured impedance Z(t) for at least a systolic period of one cardiac cycle;
   d) determining a left ventricular ejection time, $T_{LVE}$; and
   e) determining a cardiac cycle period $T_{RR}$ of the heart;
   f) calculating an approximate value of the stroke volume according to a formula $$SV = V_{EFF} \cdot C_1 \cdot \left(\frac{\left|\left(\frac{dZ(t)}{dt}\right)_{MIN}\right|}{Z_0}\right)^n \cdot \left(\frac{1}{T_{RR}}\right)^m \cdot T_{LVE}$$

wherein $0.15 < n < 0.8$ and $0 < m \leq 1.5$,
and wherein $V_{EFF}$ is an approximate value of the subject's volume of electrically participating tissue, and wherein $C_1$ is a constant.

43. The method of claim 42, wherein m is non-zero.
44. The method of claim 42, wherein $0.3 < n < 0.65$.
45. The method of claim 42, wherein $0.45 < n < 0.55$.
46. The method of claim 42, wherein $m = 1-n$.
47. The method of claim 42, wherein $C_1 = 1$.
48. The method of claim 46, wherein $m = n = 0.5$.
49. The method of claim 42, wherein $$V_{EFF} = \frac{C_3 \cdot W^X}{m Z_T^N}$$

(in milliliter),
wherein W is the subject's weight in kilogram (kg),
wherein $C_3$ is a coefficient with constant value and X and N are exponents with constant values, wherein $mZ_T=1$ for $Z_0 \geq Z_C$, and $$mZ_T = \frac{Z_C^2 - Z_C Z_0 + C_2}{2Z_C^2 + Z_0^2 - 3Z_C Z_0 + C_2}$$

for $Z_0 < Z_C$, and wherein $Z_C$ is a constant, and wherein $C_2$ is a constant.

50. The apparatus of claim 49, wherein $C_2=0$.

51. The apparatus of claim 49, wherein $C_3$ is a value in the range of 0.01–15.

52. The apparatus of claim 51, wherein $C_3$ is approximately 13.

53. The apparatus of claim 49, wherein X is a value in the range of 0.9–1.1.

54. The apparatus of claim 53, wherein X is approximately 1.025.

55. The apparatus of claim 49, wherein N is a value comprised in the range of 1.0–2.0.

56. The apparatus of claim 55, wherein N is approximately 1.5.

57. The apparatus of claim 49, wherein $Z_C$ is a value in the range of 15–25Ω.

58. The apparatus of claim 57, wherein $Z_C$ is approximately 20Ω.

59. The apparatus of claim 42, wherein $V_{EFF}=C_3 \cdot W^X$ (in milliliter), wherein W is the subject's weight in kilogram, and wherein $C_3$ is a coefficient with a constant value and X is an exponent with constant value.

60. The apparatus of claim 59, wherein $C_3$ is a value in the range of 0.01–15.

61. The apparatus of claim 60, wherein $C_3$ is approximately 13.

62. The apparatus of claim 59, wherein X is a value in the range of 0.9–1.1.

63. The apparatus of claim 62, wherein X is approximately 1.025.

64. The method of claim 42, wherein said impedance Z(t) is measured by applying an alternating current I(t) through the part of the subject's body, measuring a voltage drop U(t) in the body caused by the application of said alternating current, and calculating said impedance Z(t) according to a formula $$Z(t) = \frac{U(t)}{I(t)}.$$

65. The method of claim 42, wherein said peak magnitude $$\left| \left( \frac{dZ(t)}{dt} \right)_{MIN} \right|$$

is determined by:
sending a signal representative of Z(t) through a high-pass filter, an output of said filter being taken to be ΔZ(t), calculating $$\frac{dZ(t)}{dt}$$

for at least the systolic period of one cardiac cycle;
determining an absolute magnitude of said derivative.

66. The method of claim 42, wherein $Z_0$ is determined by sending a signal representative of Z(t) through a low-pass filter, an output of said filter being $Z_0$.

67. The method of claim 42, wherein $T_{LVE}$ is determined by
determining by analysis of $$\frac{dZ(t)}{dt}$$

a point in time when an aortic valve opens;
a point in time when the aortic valve closes; and
and by calculating a time difference of said closing point in time and said opening point in time.

68. The method of claim 42, wherein the cardiac cycle period $T_{RR}$ is determined by analyzing at least one of the group of Z(t), Z(t), $$\frac{dZ(t)}{dt}$$

and $$\left| \left( \frac{dZ(t)}{dt} \right)_{MIN} \right|$$

for at least two consecutive cardiac cycles.

69. The method of claim 42, wherein the cardiac cycle period $T_{RR}$ is determined by
measuring an electrocardiogram, and
analyzing the measured values.

70. The method of claim 42, further comprising the step of determining an approximate value for a cardiac output CO of the subject's heart, wherein CO (in liter/minute) is determined as the product of SV (in milliliter), $$\frac{1}{T_{RR}}$$

and a constant:

$$CO = SV \cdot \frac{1}{T_{RR}} \cdot \frac{60}{1000}.$$

71. An apparatus for determining an approximate value for a stroke volume SV (in milliliter) of a subject's heart, comprising a) means for measuring an electrical admittance Y(t) of a part of the subject's body, wherein a value of said electrical admittance Y(t) changes with time t as a consequence of the beating of the heart;

b) means for determining a base admittance $Y_0$ as a part of said electrical admittance Y(t) which does not change significantly during a period of one cardiac cycle;

c) means for determining a peak magnitude $$\left( \frac{dY(t)}{dt} \right)_{MAX}$$

of a temporal derivative $$\frac{dY(t)}{dt}$$

of said electrical admittance Y(t), indicating an absolute maximum rate of change of said electrical admittance Y(t) during a systolic period of the cardiac cycle;
d) means for determining a left ventricular ejection time, $T_{LVE}$;
e) means for determining the cardiac cycle period $T_{RR}$ of the heart; and
f) means for calculating said approximate value of the stroke volume SV wherein said calculating means is adapted to evaluate a formula $$SV = V_{EFF} \cdot C_1 \cdot \left(\frac{\left(\frac{dY(t)}{dt}\right)_{MAX}}{Y_0}\right)^n \cdot \left(\frac{1}{T_{RR}}\right)^m \cdot T_{LVE}$$

wherein 0.15<n<0.8 and 0<m<1.5,
and wherein $V_{EFF}$ is an approximate value of the subject's volume of electrically participating tissue, and wherein $C_1$ is a constant.

72. The apparatus of claim 71, wherein m is non-zero.
73. The apparatus of claim 71, wherein $0.3 \leq n \leq 0.65$.
74. The apparatus of claim 71, wherein $0.45 \leq n \leq 0.55$.
75. The apparatus of claim 71, wherein m=1−n.
76. The apparatus of claim 71, wherein $C_1=1$.
77. The apparatus of claim 75, wherein m=n=0.5.
78. The apparatus of claim 71, wherein $V_{EFF}=C_3 \cdot W^X \cdot mY_T^N$ (in milliliter), wherein W is the subject's weight in kilogram (kg), wherein $C_3$ is a coefficient with constant value and X and N are exponents with constant values, wherein $mY_T=1$ for $Y_0 \leq Y_C$, and $$mY_T = \frac{2Y_0^2 + Y_C^2 - 3Y_C Y_0 + C_2}{Y_0^2 - Y_C Y_0 + C_2}$$

for $Y_0 > Y_C$, and wherein $Y_C$ is a constant, and wherein $C_2$ is a constant.

79. The apparatus of claim 78, wherein $C_2=0$.
80. The apparatus of claim 78, wherein $C_3$ is a value in the range of 0.01–15.
81. The apparatus of claim 80, wherein $C_3$ is approximately 13.
82. The apparatus of claim 78, wherein X is a value in the range of 0.9–1.1.
83. The apparatus of claim 82, wherein X is approximately 1.025.
84. The apparatus of claim 78, wherein N is a value in the range of 1.0–2.0.
85. The apparatus of claim 84, wherein N is approximately 1.5.
86. The apparatus of claim 78, wherein $Y_C$ is a value in the range of 0.04–0.0667 $\Omega^{-1}$.
87. The apparatus of claim 86, wherein $Y_C$ is approximately 0.05 $\Omega^{-1}$.
88. The apparatus of claim 71, wherein $V_{EFF}=C_3 \cdot W^X$ (in milliliter), wherein W is the subject's weight in kilogram, and wherein $C_3$ is a coefficient with a constant value and X is an exponent with constant value.
89. The apparatus of claim 88, wherein $C_3$ is a value in the range of 0.01–15.
90. The apparatus of claim 89, wherein $C_3$ is approximately 13.
91. The apparatus of claim 88, wherein X is a value in the range of 0.9–1.1.
92. The apparatus of claim 91, wherein X is approximately 1.025.
93. The apparatus of claim 71, wherein said means for measuring said electrical admittance Y(t) comprises:
   at least two pairs of electrodes;
   a current source generating an alternating current I(t) of predetermined amplitude;
   wherein one pair of electrodes is adapted to be connected to said current source;
   means for measuring a voltage U(t) caused by applying said alternating current;
   wherein one pair of electrodes is connected to said means for measuring the voltage U(t);
   means for determining said electrical admittance Y(t) from the voltage U(t) and the current I(t).
94. The apparatus of claim 71, wherein said means for determining the peak magnitude $$\left(\frac{dY(t)}{dt}\right)_{MAX}$$

comprises:
   means for determining $\Delta Y(t)$ from Y(t);
   means for calculating $$\frac{dY(t)}{dt}$$

for at least the systolic period of one cardiac cycle;
   means for determining the maximum of an input function.
95. The apparatus of claim 94, wherein said means for determining $\Delta Y(t)$ is a high-pass filter.
96. The apparatus of claim 71, wherein said means for determining $Y_0$ is a low-pass filter.
97. The apparatus of claim 71, wherein said means for determining $T_{LVE}$ determines $T_{LVE}$ by determining by analysis of $$\frac{dY(t)}{dt}$$

a point in time when an aortic valve opens;
   a point in time when the aortic valve closes;
   and by calculating a time difference of said closing point in time and said opening point in time.
98. The apparatus of claim 71, wherein said means for determining the cardiac cycle period $T_{RR}$ comprises means for analyzing at least one of a group of Y(t), $\Delta Y(t)$, $$\frac{dY(t)}{dt}$$

and $$\left(\frac{dY(t)}{dt}\right)_{MAX}.$$

99. The apparatus of claim 71, wherein said means for determining the cardiac cycle period $T_{RR}$ comprises means for measuring an electrocardiogram and means for analyzing the measured values.

100. The apparatus of claim 71, wherein at least one of said means for determining $$\left(\frac{dY(t)}{dt}\right)_{MAX},$$

$Y_0$, $T_{LVE}$ and $T_{RR}$ and said means for calculating are comprised in a processing unit.

101. The apparatus of claim 71, further comprising means for outputting a signal, which is representative of SV.

102. The apparatus of claim 71, further comprising means for visually displaying SV to a user.

103. The apparatus of claim 71, further comprising means for calculating an approximate value for a cardiac output CO of the subject's heart (in liter/minute), wherein said calculating means is adapted to evaluate a formula $$CO = SV \cdot \frac{1}{T_{RR}} \cdot \frac{60}{1000}.$$

104. An apparatus for determining an approximate value for a stroke volume SV of a subject's heart, comprising a) a current source outputting an alternating current I(t) of predetermined amplitude to two electrodes;

b) means for measuring a voltage U(t) caused by said alternating current between two electrodes; and c) a processing unit receiving at least a signal representative of U(t), said processing unit being adapted to:

calculate an admittance Y(t) from the voltage U(t) and a value of the current I(t);

input Y(t) into a low-pass filter, an output of said low-pass filter being $Y_0$;

input Y(t) into a high-pass filter, an output of said high-pass filter being $\Delta Y(t)$;

calculate a peak magnitude $$\left(\frac{dY(t)}{dt}\right)_{MAX}$$

of $$\frac{dY(t)}{dt};$$

determine a left ventricular ejection time $T_{LVE}$ from at least one of Y(t), $\Delta Y(t)$ and $$\frac{dY(t)}{dt}$$

by using predetermined criteria;
determine a cardiac cycle period $T_{RR}$ of the heart from at least one of Y(t), $\Delta Y(t)$ and $$\frac{dY(t)}{dt}$$

by using predetermined criteria;

calculate SV according to a formula $$SV = V_{EFF} \cdot C_1 \cdot \left(\frac{\left(\frac{dY(t)}{dt}\right)_{MAX}}{Y_0}\right)^n \cdot \left(\frac{1}{T_{RR}}\right)^m \cdot T_{LVE}$$

wherein $0.15 \leq n \leq 0.8$ and $0 < m \leq 1.5$,
and wherein $V_{EFF}$ is an approximate value of the subject's volume of electrically participating tissue, and wherein $C_1$ is a constant.

105. The apparatus of claim 104, wherein n=m=0.5, and wherein $C_1=1$.

106. An apparatus for determining an approximate value for the stroke volume SV of a subject's heart, comprising a) a current source outputting an alternating current I(t) of predetermined amplitude to two electrodes;

b) means for measuring a voltage U(t) caused by said alternating current between two electrodes;

c) means for measuring an electrocardiogram; and d) a processing unit receiving at least a signal representative of U(t) and measured values of said electrocardiogram, said processing unit being adapted to:

calculate an admittance Y(t) from the voltage U(t) and a value of the current I(t);

input Y(t) into a low-pass filter, an output of said low-pass filter being $Y_0$;

input Y(t) into a high-pass filter, an output of said high-pass filter being $\Delta Y(t)$;

calculate a peak magnitude $$\left(\frac{dY(t)}{dt}\right)_{MAX}$$

of $$\frac{dY(t)}{dt};$$

determine a left ventricular ejection time $T_{LVE}$ from at least one of Y(t), $\Delta Y(t)$ and $$\frac{dY(t)}{dt}$$

by using predetermined criteria;
determine a cardiac cycle period $T_{RR}$ of the heart from the measured values of said electrocardiogram;
calculate SV according to a formula $$SV = V_{EFF} \cdot C_1 \cdot \left(\frac{\left(\frac{dY(t)}{dt}\right)_{MAX}}{Y_0}\right)^n \cdot \left(\frac{1}{T_{RR}}\right)^m \cdot T_{LVE}$$

wherein $0.15 < n < 0.8$ and $0 < m \leq 1.5$,
and wherein $V_{EFF}$ is an approximate value of the subject's volume of electrically participating tissue, and wherein $C_1$ is a constant.

107. The apparatus of claim 106, wherein n=m =0.5, and wherein $C_1=1$.

108. An apparatus for determining an approximate value for a stroke volume SV of a subject's heart, comprising a) a current source outputting an alternating current I(t) of predetermined amplitude to two electrodes;

b) means for measuring a voltage U(t) caused by said alternating current between two electrodes;

c) means for measuring an electrocardiogram and means for calculating a cardiac cycle period $T_{RR}$ of the heart from measured values of said electrocardiogram;

d) a processing unit receiving at least a signal representative of U(t) and a signal representative of $T_{RR}$, said processing unit being adapted to:

calculate an admittance Y(t) from the voltage U(t) and a value of the current I(t);

input Y(t) into a low-pass filter, an output of said low-pass filter being $Y_0$;

input Y(t) into a high-pass filter, an output of said high-pass filter being $\Delta Y(t)$;

calculate a peak magnitude $$\left(\frac{dY(t)}{dt}\right)_{MAX}$$

of $$\frac{dY(t)}{dt};$$

determine a left ventricular ejection time $T_{LVE}$ from at least one of Y(t), $\Delta Y(t)$ and $$\frac{dY(t)}{dt}$$

by using predetermined criteria;

calculate SV according to a formula $$SV = V_{EFF} \cdot C_1 \cdot \left(\frac{\left(\frac{dY(t)}{dt}\right)_{MAX}}{Y_0}\right)^n \cdot \left(\frac{1}{T_{RR}}\right)^m \cdot T_{LVE}$$

wherein $0.15 < n < 0.8$ and $0 < m \leq 1.5$, and wherein $V_{EFF}$ is an approximate value of the subject's volume of electrically participating tissue, and wherein $C_1$ is a constant.

109. The apparatus of claim 108, wherein said means for calculating the cardiac cycle period $T_{RR}$ is adapted to output a signal representative of $T_{RR}$ to the processing unit.

110. The apparatus of claim 108 wherein n=m=0.5, and wherein $C_1=1$.

111. An apparatus for determining an approximate value for a stroke volume SV of a subject's heart, comprising a) a current source outputting an alternating current I(t) of predetermined amplitude to two electrodes;

b) means for measuring a voltage U(t) caused by said alternating current between two electrodes;

c) a processor unit receiving at least a signal representative of U(t), said processing unit being adapted to:

calculate an admittance Y(t) from the voltage U(t) and a value of the current I(t);

input Y(t) into a low-pass filter, an output of said low-pass filter being $Y_0$;

input Y(t) into a high-pass filter, an output of said high-pass filter being $\Delta Y(t)$;

calculate a peak magnitude $$\left(\frac{dY(t)}{dt}\right)_{MAX}$$

of $$\frac{dY(t)}{dt};$$

determine a left ventricular ejection time $T_{LVE}$ from at least one of Y(t), $\Delta Y(t)$ and $$\frac{dY(t)}{dt}$$

by using predetermined criteria;

calculate SV according to a formula $$SV = V_{EFF} \cdot C_1 \cdot \left(\frac{\left(\frac{dY(t)}{dt}\right)_{MAX}}{Y_0}\right)^n \cdot T_{LVE}$$

wherein $0.15 < n < 0.8$, and wherein $V_{EFF}$ is an approximate value of the subject's volume of electrically participating tissue, and wherein $C_1$ is a constant.

112. A method of determining an approximate value for a stroke volume SV of a subject's heart, comprising the steps of:

a) measuring an admittance Y(t) of a part of the subject's body, wherein a value of said admittance Y(t) changes with time t as a consequence of the beating of the heart;

b) determining a mean admittance $Y_0$;

c) determining a peak magnitude $$\left(\frac{dY(t)}{dt}\right)_{MAX}$$

of a derivative $$\frac{dY(t)}{dt}$$

of said admittance Y(t) over the time t by using the measured admittance Y(t) for at least a systolic period of one cardiac cycle;

d) determining a left ventricular ejection time, $T_{LVE}$; and e) determining a cardiac cycle period $T_{RR}$ of the heart;

f) calculating an approximate value of the stroke volume according to a formula $$SV = V_{EFF} \cdot C_1 \cdot \left(\frac{\left(\frac{dY(t)}{dt}\right)_{MAX}}{Y_0}\right)^n \cdot \left(\frac{1}{T_{RR}}\right)^m \cdot T_{LVE}$$

wherein $0.15 < n < 0.8$ and $0 < m \leq 1.5$, and wherein $V_{EFF}$ is an approximate value of the subject's volume of electrically participating tissue, and wherein $C_1$ is a constant.

113. The method of claim 112, wherein m is non-zero.

114. The method of claim 112, wherein $0.3 < n < 0.65$.

115. The method of claim 112, wherein $0.45<n<0.55$.

116. The method of claim 112, wherein $m=1-n$.

117. The method of claim 112, wherein $C_1=1$.

118. The method of claim 116, wherein $m=n=0.5$.

119. The method of claim 112, wherein $V_{EFF}=C_3 \cdot W^X \cdot mY_T^N$ (in milliliter), wherein W is the subject's weight in kilogram (kg), wherein $C_3$ is a coefficient with constant value and X and N are exponents with constant values, wherein $mY_T=1$ for $Y_0 \leq Y_C$, and $$mY_T = \frac{2Y_0^2 + Y_C^2 - 3Y_C Y_0 + C_2}{Y_0^2 - Y_C Y_0 + C_2}$$

for $Y_0 > Y_C$, and wherein $Y_C$ is a constant, and wherein $C_2$ is a constant.

120. The apparatus of claim 119, wherein $C_2=0$.

121. The apparatus of claim 119, wherein $C_3$ is a value in the range of 0.01–15.

122. The apparatus of claim 121, wherein $C_3$ is approximately 13.

123. The apparatus of claim 119, wherein X is a value in the range of 0.9–1.1.

124. The apparatus of claim 123, wherein X is approximately 1.025.

125. The apparatus of claim 119, wherein N is a value comprised in the range of 1.0–2.0.

126. The apparatus of claim 125, wherein N is approximately 1.5.

127. The apparatus of claim 119, wherein $Y_C$ is a value in the range of 0.04–0.0667 $\Omega^{-1}$.

128. The apparatus of claim 127, wherein $Y_C$ is approximately 0.05 $\Omega^{-1}$.

129. The apparatus of claim 112, wherein $V_{EFF}=C_3 \sim W^X$ (in milliliter), wherein W is the subject's weight in kilogram, and wherein $C_3$ is a coefficient with a constant value and X is an exponent with constant value.

130. The apparatus of claim 129, wherein $C_3$ is a value in the range of 0.01–15.

131. The apparatus of claim 130, wherein $C_3$ is approximately 13.

132. The apparatus of claim 129, wherein X is a value in the range of 0.9–1.1.

133. The apparatus of claim 132, wherein X is approximately 1.025.

134. The method of claim 112, wherein said admittance Y(t) is measured by applying an alternating current I(t) through the part of the subject's body, measuring a voltage drop U(t) in the body caused by the application of said alternating current, and calculating said admittance Y(t) according to a formula $$Y(t) = \frac{I(t)}{U(t)}.$$

135. The method of claim 112, wherein said peak magnitude $$\left(\frac{dY(t)}{dt}\right)_{MAX}$$

is determined by:

sending a signal representative of Y(t) through a high-pass filter, an output of said filter being taken to be $\Delta Y(t)$, calculating $$\frac{dY(t)}{dt}$$

for at least the systolic period of one cardiac cycle;

determining an absolute magnitude of said derivative.

136. The method of claim 112, wherein $Y_0$ is determined by sending a signal representative of Y(t) through a low-pass filter, an output of said filter being $Y_0$.

137. The method of claim 112, wherein $T_{LVE}$ is determined by determining by analysis of $$\frac{dY(t)}{dt}$$

a point in time when an aortic valve opens;

a point in time when the aortic valve closes; and and by calculating a time difference of said closing point in time and said opening point in time.

138. The method of claim 112, wherein the cardiac cycle period $T_{RR}$ is determined by analyzing at least one of the group of Y(t), $\Delta Y(t)$, $$\frac{dY(t)}{dt}$$

and $$\left(\frac{dY(t)}{dt}\right)_{MAX}$$

for at least two consecutive cardiac cycles.

139. The method of claim 112, wherein the cardiac cycle period $T_{RR}$ is determined by measuring an electrocardiogram, and analyzing the measured values.

140. The method of claim 112, further comprising the step of determining an approximate value for a cardiac output CO of the subject's heart, wherein CO (in liter/minute) is determined as the product of SV (in milliliter), $$\frac{1}{T_{RR}}$$

and a constant:

$$CO = SV \cdot \frac{1}{T_{RR}} \cdot \frac{60}{1000}.$$

* * * * *

UNITED STATES PATENT AND TRADEMARK OFFICE
CERTIFICATE OF CORRECTION

PATENT NO. : 6,511,438 B2
DATED : January 28, 2003
INVENTOR(S) : Donald P. Bernstein et al.

It is certified that error appears in the above-identified patent and that said Letters Patent is hereby corrected as shown below:

<u>Title page,</u>
Item [57], ABSTRACT,
Line 1, change "The invention relates to an" to -- An --.

<u>Column 24,</u>
Line 11, change "Z(t), Z(t)" to -- Z(t), ΔZ(t) --.

<u>Column 25,</u>
Line 14, change "<" (all occurrences) to -- ≤ --.

<u>Column 31,</u>
Line 30, change "$V_{EFF}=C_3 \sim W^X$" to -- $V_{EFF}=C_3 \cdot W^X$ --.

Signed and Sealed this

Second Day of December, 2003

JAMES E. ROGAN
*Director of the United States Patent and Trademark Office*